United States Patent

Okada et al.

Patent Number: 5,530,019
Date of Patent: Jun. 25, 1996

[54] INDOLE DERIVATIVES USEFUL AS TESTOSTERONE 5α-REDUCTASE INHIBITORS

[75] Inventors: Satoshi Okada, Souraku-gun; Kozo Sawada, Tsukuba; Akio Kuroda, Uji; Shinya Watanabe, Tsukuba; Hirokazu Tanaka, Takarazuka, all of Japan

[73] Assignee: Fujisawa Pharmaceutical Co., Ltd., Osaka, Japan

[21] Appl. No.: 338,533

[22] PCT Filed: Mar. 14, 1994

[86] PCT No.: PCT/JP94/00406

§ 371 Date: Mar. 8, 1995

§ 102(e) Date: Mar. 8, 1995

[87] PCT Pub. No.: WO94/22821

PCT Pub. Date: Oct. 13, 1994

[30] Foreign Application Priority Data

Apr. 5, 1993 [GB] United Kingdom ............ 9307080
May 4, 1993 [GB] United Kingdom ............ 9309148

[51] Int. Cl.$^6$ .................. A61K 31/40; C07D 209/12
[52] U.S. Cl. .................. 514/419; 548/492; 548/493
[58] Field of Search ............ 514/419; 548/492, 548/493

[56] References Cited

FOREIGN PATENT DOCUMENTS 746518  11/1966  Canada ...................... 548/493
458207  11/1991  European Pat. Off. ...... C07D 209/12
93/02051 2/1993  WIPO ........................ C07D 209/42

*Primary Examiner*—Jacqueline Haley
*Attorney, Agent, or Firm*—Oblon, Spivak, McClelland, Maier & Neustadt

[57] ABSTRACT

A compound of the formula (I):

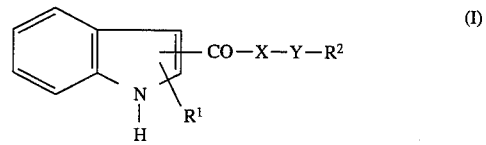

wherein $R^1$ is an optionally protected carboxy(lower)alkyl,
$R^2$ is a hydrogen, an optionally substituted aryl or a carboxy,
X is a bond, —O—, —NH— or a cycloalkylene, and
Y is an alkylene which may be interrupted by an oxygen atom, an alkenylene or an alkadienylene, or a pharmaceutically acceptable salt thereof. The compound of the present invention is useful as a testosterone 5α-reductase inhibitor and effective against testosterone 5α-reductase-mediated diseases such as prostatism, prostatic hypertrophy, prostatic cancer, alopecia, hirsutism (e.g. female hirsutism), androgenic alopecia (or male-pattern baldness), acne (e.g. acne vulgaris, pimple), and other hyperandrogenisms.

4 Claims, No Drawings

INDOLE DERIVATIVES USEFUL AS TESTOSTERONE 5α-REDUCTASE INHIBITORS

This application is a National Stage application of PCT/JP94/00406, filed Mar. 14, 1994, which published as WO94/22821 on Oct. 13, 1994.

TECHNICAL FIELD

The present invention relates to novel indole derivatives and pharmaceutically acceptable salts thereof. More particularly, it relates to novel indole derivatives and pharmaceutically acceptable salts thereof, which have pharmacological activities such as inhibitory activity on testosterone 5α-reductase, to a process for the preparation thereof, to a pharmaceutical composition comprising the same, and to a use of the same as a medicament.

BACKGROUND ART

It has hitherto been known that indole derivatives are effective for testosterone 5α-reductase-mediated diseases. However, a testosterone 5α-reductase inhibitor with stronger effect has been demanded.

DISCLOSURE OF THE INVENTION

Accordingly, one object of the present invention is to provide novel indole derivatives and pharmaceutically acceptable salts thereof, which are useful as a testosterone 5α-reductase inhibitor.

Another object of the present invention is to provide a process for the preparation of said indole derivatives or salts thereof.

A further object of the present invention is to provide a pharmaceutical composition comprising, as an active ingredient, said indole derivative or a pharmaceutically acceptable salt thereof.

A still further object of the present invention is to provide use of said indole derivatives or pharmaceutically acceptable salts thereof as a medicament such as a testosterone 5α-reductase inhibitor useful for treating and/or preventing testosterone 5α-reductase-mediated diseases such as alopecia, acnes and prostatism in human being or animals.

Indole derivatives of the present invention are novel and can be represented by the formula (I):

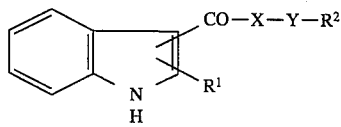

wherein $R^1$ is an optionally protected carboxy(lower)alkyl, $R^2$ is a hydrogen, an optionally substituted aryl or a carboxy, X is a bond, —O—, —NH—, or a cycloalkylene, and Y is an alkylene which may be interrupted by an oxygen atom, an alkenylene or an alkadienylene.

According to the present invention, the object compound (I) and a salt thereof can be prepared by the following processes.

[Process 1]

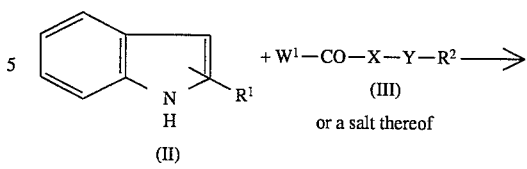

[Process 2]

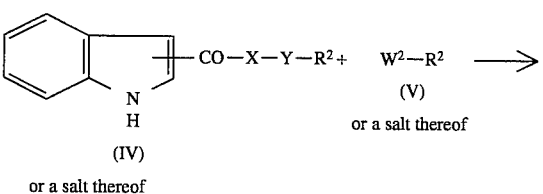

[Process 3]

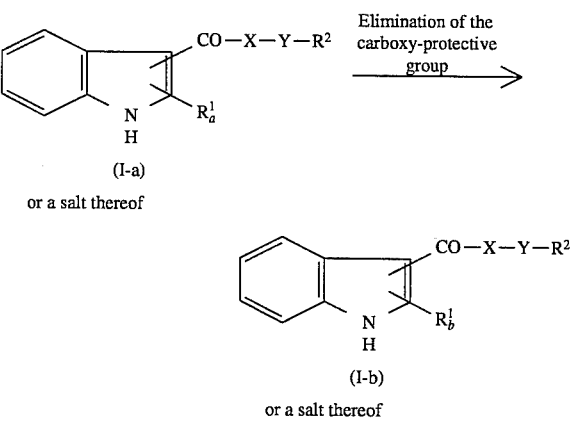

wherein each of $R^1$, $R^2$, X and Y is as defined above, $R_a^1$ is a protected carboxy(lower)alkyl, $R_b^1$ is a carboxy(lower)alkyl, $W^1$ is a leaving group and $W^2$ is an acid residue.

Suitable salts of the compound (I) are conventional, nontoxic, pharmaceutically acceptable salts, and include salts with base or acid addition salts. There are exemplified salts with inorganic bases such as alkali metal salts (e.g. sodium salt, potassium salt, cesium salt), alkaline earth metal salts (e.g. calcium salt, magnesium salt) and ammonium salts; salts with organic bases such as organic amine salts (e.g. triethylamine salt, pyridine salt, picoline salt, ethanolamine salt, triethanolamine salt, dicyclohexylamine salt, N,N'-dibenzylethylenediamine salt); inorganic acid addition salts (e.g. hydrochloride, hydrobromide, sulfate, phosphate); organic carboxylic or sulfonic acid addition salts (e.g. formate, acetate, trifluoroacetate, maleate, tartrate, methanesulfonate, benzenesulfonate, p-toluenesulfonate); and salts with basic or acidic amino acids (e.g. arginine, aspartic acid, glutamic acid). The preferable salts are acid addition salts.

Suitable examples of the salts of the compounds (I-a), (I-b), (II), (III), (IV) and (V) in Processes 1 to 3 are to be referred to those as exemplified for the object compound (I).

In the above and subsequent descriptions of the present specification, suitable examples and illustrations of the various definitions which the present invention includes within the scope thereof are detailed as follows:

The term "lower" means that the number of carbon atoms is from 1 to 6, preferably 1 to 4, unless otherwise indicated.

Suitable "lower alkyl" includes straight or branched ones having 1 to 6 carbon atoms, such as methyl, ethyl, propyl, isopropyl, butyl, isobutyl, t-butyl, pentyl and hexyl, preferable ones having 1 to 4 carbon atoms.

"Carboxy(lower)alkyl" means a lower alkyl as explained above, which is substituted by a carboxyl group at optional position(s). Examples of the suitable "carboxy(lower)alkyl" are carboxymethyl, carboxyethyl, carboxypropyl, carboxybutyl, carboxypentyl and carboxyhexyl. Preferred is carboxy($C_1$–$C_4$) alkyl and the most preferred is 3-carboxypropyl.

"Protected carboxy(lower)alkyl" means a carboxy(lower)alkyl as explained above, in which the carboxyl group is protected by a conventional carboxy-protective group, and suitable "protected carboxy" moiety of "protected carboxy(lower)alkyl" includes an esterified carboxyl group.

Suitable examples of the ester moiety of "esterified carboxy" are lower alkyl ester (e.g. methyl ester, ethyl ester, propyl ester, isopropyl ester, butyl ester, isobutyl ester, tert-butyl ester, pentyl ester, hexyl ester, 1-cyclopropylethyl ester) which may have one or more suitable substituents such as lower alkanoyloxy(lower)alkyl ester [e.g. acetoxymethyl ester, propionyloxymethyl ester, butyryloxymethyl ester, valeryloxymethyl ester, pivaloyloxymethyl ester, hexanoyloxymethyl ester, 1(or 2)-acetoxyethyl ester, 1(or 2 or 3)-acetoxypropyl ester, 1(or 2 or 3 or 4)-acetoxybutyl ester, 1(or 2)propionyloxyethyl ester, 1(or 2 or 3)-propionyloxypropyl ester, 1(or 2)-butyryloxyethyl ester, 1(or 2)-isobutyryloxyethyl ester, 1(or 2)-pivaloyloxyethyl ester, 1(or 2)-hexanoyloxyethyl ester, 3,3-dimethylbutyryloxymethyl ester, 1(or 2)-pentanoyloxyethyl ester], lower alkanesulfonyl(lower)alkyl ester [e.g. 2-mesylethyl ester], mono(or di or tri)-halo(lower)alkyl ester [e.g. 2-iodoethyl ester, 2,2,2-trichloroethyl ester], lower alkoxycarbonyloxy(lower)alkyl ester [e.g. methoxycarbonyloxymethyl ester, ethoxycarbonyloxymethyl ester, 2-methoxycarbonyloxyethyl ester, 1-ethoxycarbonyloxyethyl ester, 1-isopropoxycarbonyloxyethyl ester], phthalidylidene(lower)alkyl ester, or (5-lower alkyl-2-oxo-1,3-dioxol-4-yl)(lower)alkyl ester [e.g. (5-methyl2-oxo-1,3-dioxol-4-yl)methyl ester, (5-ethyl-2-oxo-1,3-dioxol-4yl)methyl ester, (5-propyl-2-oxo-1,3-dioxol-4-yl)ethyl ester]; lower alkenyl ester [e.g. vinyl ester, allyl ester]; lower alkynyl ester [e.g. ethynyl ester, propynyl ester]; ar(lower)alkyl ester which may have one or more suitable substituents [e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3, 5-di-tert-butylbenzyl ester]; aryl ester which may have one or more suitable substituents [e.g. phenyl ester, 4-chlorophenyl ester, tolyl ester, tert-butylphenyl ester, xylyl ester, mesityl ester, cumenyl ester]; and phthalidyl ester.

Examples of the preferable esterified carboxy as mentioned above include lower alkoxycarbonyl (e.g. methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, tert-pentyloxycarbonyl, hexyloxycarbonyl, 1-cyclopropylethoxycarbonyl).

"Alkadienylene" preferably has from 6 to 24 carbon atoms, and more preferably from 6 to 18 carbon atoms.

Suitable "alkadienylene" includes heptadecadienylene.

Suitable "optionally substituted aryl" includes aryl such as phenyl and naphthyl, and substituted aryl such as lower alkylphenyl (e.g. tolyl, xylyl, mesityl, cumenyl, isobutylphenyl), lower alkoxyphenyl (e.g. methoxyphenyl) and halophenyl (e.g. chlorophenyl).

"Alkylene" is a straight or branched bivalent alkane having 2 to 24, preferably 4 to 18, more preferably 4 to 16 carbon atoms.

Suitable "alkylene" includes ethylene, trimethylene, tetramethylene, pentamethylene, hexamethylene, heptamethylene, octamethylene, nonamethylene, decamethylene, undecamethylene, dodecamethylene, tridecamethylene, tetradecamethylene, pentadecamethylene, hexadecamethylene, heptadecamethylene, octadecamethylene, nonadecamethylene, icosamethylene, henicosamethylene, docosamethylene, tricosamethylene, tetracosamethylene, pentacosamethylene, hexacosamethylene, heptacosamethylene, octacosamethylene, propylene, butylpentamethylene, methyltetramethylene and butylnonamethylene.

"Alkenylene" is a straight or branched bivalent alkene having 2 to 24, preferably 2 to 18, more preferably 2 to 16 carbon atoms.

Suitable "alkenylene" includes vinylene, propenylene, butenylene, pentenylene, hexenylene, heptenylene, octenylene, nonenylene, decenylene, dimethylheptenylene, methyldecenylene and heptylnonenylene.

"Cycloalkylene" is a bivalent cycloalkane having 3 to 12, preferably 3 to 8 carbon atoms.

Suitable "cycloalkylene" includes cyclopropylene, cyclobutylene, cyclopentylene, cyclohexylene, cycloheptylene, cyclooctylene, cyclononylene, cyclodecylene, cycloundecylene and cyclododecylene.

Suitable "leaving group" includes hydroxyl, and reactive groups derived from hydroxyl.

Suitable "reactive group derived from hydroxyl" includes acid residues.

Suitable "acid residue" includes halogen (e.g. fluoro, chloro, bromo, iodo) and acyloxy (e.g. acetoxy, tosyloxy, mesyloxy).

Particularly, the preferred embodiments of $R^1$, $R^2$, X and Y are as follows:

$R^1$: carboxy(lower)alkyl and lower alkoxycarbonyl(lower)alkyl, $R^2$: hydrogen, phenyl, lower alkylphenyl, lower alkoxyphenyl and carboxy, X: bond, —O—, —NH— and cyclo($C_3$–$C_6$)alkylene, and y: ($C_4$–$C_{16}$)alkylene which may be interrupted by oxygen atom, ($C_2$–$C_{16}$)alkenylene and ($C_6$–$C_{18}$)alkadienylene.

Most preferable compounds of the compound (I) are represented by the following formula:

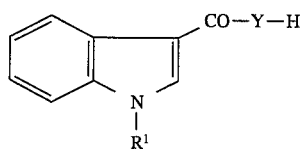

wherein $R^1$ is a carboxy(lower)alkyl, and
$Y$ is a $(C_4-C_{16})$alkylene.

The processes 1 to 3 for preparing the object compound (I) of the present invention are explained in detail in the following.

Process 1

The object compound (I) and a salt thereof can be prepared by reacting the compound (II) or a salt thereof with the compound (III) or a salt thereof.

Suitable salts of the compounds (II) and (III) can be referred to the ones as exemplified for the compound (I).

This reaction is usually carried out in a solvent such as an alcohol [e.g. methanol, ethanol], dichloromethane, benzene, N,N-dimethylformamide, tetrahydrofuran, diethyl ether, toluene, or any other solvent which does not adversely affect the reaction. These solvents may be used alone or upon mixing with one another.

In this reaction, when $W^1$ in the compound (III) is an acid residue, the reaction may be carried out in the presence of an inorganic or organic base. Examples of the base are alkali metal hydroxides [e.g. sodium hydroxide, potassium hydroxide], alkali metal carbonates [e.g. sodium carbonate, potassium carbonate], alkali metal bicarbonates [e.g. sodium bicarbonate, potassium bicarbonate], alkali metal hydrides [e.g. sodium hydride, potassium hydride], tri(lower)alkylamines [e.g. trimethylamine, triethylamine, diisopropylethylamine], and pyridine and its derivatives [e.g. picoline, lutidine, 4-dimethylaminopyridine]. In case where the base to be used is a liquid, it can also be used as a solvent.

When $W^1$ in the compound (III) is hydroxyl, this reaction is usually carried out in the presence of a conventional condensing agent. Examples of the condensing agent are N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide; N,N'-diisopropylcarbodiimide; N-ethyl-N'-(3-dimethylaminopropyl)carbodiimide; N,N'-carbonylbis(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; thionyl chloride; oxalyl chloride; lower alkyl haloformate [e.g. ethyl chloroformate, isopropyl chloroformate]; a combination of triarylphosphine [e.g. triphenylphosphine]or tri(lower)alkylphosphine [e.g. triethylphosphine], and di(lower)alkyl azodicarboxylate [e.g. diethyl azodicarboxylate]; 2-ethyl-7-hydroxybenzisoxazolium salt; 2-ethyl-5-(m-sulfophenyl)isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride; phosgene; trichloromethyl chloroformate; and phosphorus oxychloride.

The reaction temperature is not critical, and the reaction can be carried out under cooling, at room temperature or under warming or heating.

Process 2

The object compound (I) and a salt thereof can be prepared by reacting the compound (IV) or a salt thereof with the compound (V) or a salt thereof.

This reaction can be carried out in substantially the same manner as Process 1, and therefore the reaction mode and reaction conditions [e.g. solvents, reaction temperature]of this reaction are to be refefred to those as explained in Process 1.

Process 3

The object compound (I-b) and a salt thereof can be prepared by subjecting the compound (I-a) or a salt thereof to an elimination reaction of the carboxy-protective group.

In the present elimination reaction, all conventional methods used for the elimination of carboxy-protective group, for example, hydrolysis, reduction, elimination using a Lewis acid, etc. are applicable. When the carboxy-protective group is an ester, it can be eliminated by hydrolysis or elimination using a Lewis acid. The hydrolysis is preferably carried out in the presence of a base or an acid.

Suitable base includes, for example, inorganic bases such as alkali metal hydroxides (e.g. sodium hydroxide, potassium hydroxide), alkaline earth metal hydroxides (e.g. magnesium hydroxide, calcium hydroxide), alkali metal carbonates (e.g. sodium carbonate, potassium carbonate), alkaline earth metal carbonates (e.g. magnesium carbonate, calcium carbonate), alkali metal bicarbonates (e.g. sodium bicarbonate, potassium bicarbonate), alkali metal acetates (e.g. sodium acetate, potassium acetate), alkaline earth metal phosphates (e.g. magnesium phosphate, calcium phosphate), and alkali metal hydrogen phosphates (e.g. disodium hydrogen phosphate, dipotassium hydrogen phosphate); and organic bases such as trialkylamines (e.g. trimethylamine, triethylamine), picoline, N-methylpyrrolidine, N-methylmorpholine, and 1,5-diazabicyclo-[4.3.0]non-5-one, 1,4-diazabicyclo[2.2.21]octane, and 1,5-diazabicyclo[5.4.0]undecene-5. The hydrolysis using a base is often carried out in water, hydrophilic organic solvents or mixed solvents thereof.

Suitable acid includes organic acids (e.g. formic acid, acetic acid, propionic acid) and inorganic acids (e.g. hydrochloric acid, hydrobromic acid, sulfuric acid). The present hydrolysis is usually carried out in organic solvents, water or mixed solvents thereof.

The reaction temperature is not critical, and it may be selected suitably in accordance with the kind of carboxy-protective group and elimination method.

The elimination using a Lewis acid is preferable for eliminating a substituted or unsubstituted ar(lower)alkyl ester, and carried out by reacting the compound (I-a) or a salt thereof with a Lewis acid. Examples of the Lewis acid are boron trihalides (e.g. boron trichloride, boron trifluoride), titanium tetrahalides (e.g. titanium tetrachloride, titanium tetrabromide), tin tetrahalides (e.g. tin tetrachloride, tin tetrabromide), aluminum halides (e.g. aluminum chloride, aluminum bromide), and trihaloacetic acids (e.g. trichloroacetic acid, trifluoroacetic acid). This elimination reaction is preferably carried out in the presence of cation trapping agent (e.g. anisole, phenol) and is usually carried out in a solvent such as nitroalkane (e.g. nitromethane, nitroethane), alkylene halide (e.g. methylene chloride, ethylene chloride), diethyl ether, carbon disulfide or any other solvent which does not adversely affect the reaction. These solvents may be used alone or upon mixing with one another.

The reduction elimination can be preferably conducted for eliminating a protective group such as halo(lower)alkyl (e.g. 2-iodoethyl, 2,2,2-trichloroethyl) ester, and ar(lower)alkyl (e.g. benzyl) ester.

The reduction applicable for the elimination reaction includes reduction using a combination of a metal (e.g. zinc, zinc amalgam) or salt of chromium compound (e.g. chromous chloride, chromous acetate) and an organic or inorganic acid (e.g. acetic acid, propionic acid, hydrochloric acid); and conventional catalytic reduction in the presence of a conventional metallic catalyst (e.g. palladium carbon, Raney nickel).

The reaction temperature is not critical, and the reaction is usually carried out under cooling, at ambient temperature or under warming.

The starting compound (IV) includes novel compounds which can be prepared by the following methods or in a conventional manner. The details of the following methods and conventional ones are shown in Preparation Examples to be mentioned below.

Method A

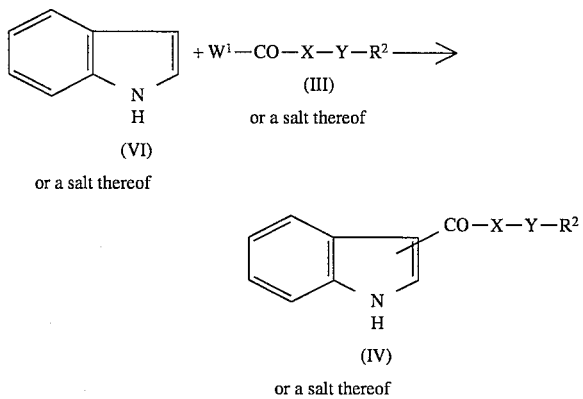

wherein $R^2$, X, Y and $W^1$ are each as defined above.

Method A can be carried out in a conventional manner.

The object compound (I) of the present invention can be isolated and purified in a conventional manner by extraction, precipitation, fractional crystallization, recrystallization, or chromatography.

The object compound (I) thus obtained can be converted to its salt by a conventional method.

The object compound (I) of the present invention is useful as a testosterone 5α-reductase inhibitor and effective for testosterone 5α-reductase mediated diseases such as prostatism, prostatic hypertrophy, prostatic cancer, alopecia, hirsutism (e.g. female hirsutism), androgenic alopecia (or malepattern baldness), ache (e.g. ache vulgaris, pimple), other hyperandrogenism, and the like.

In order to illustrate the usefulness of the object compounds (I), pharmacological activity of representative compound of the present invention is shown below.
[1] Test Compound:
(1) 4-(3-Undecanoyl-1-indolyl)butyric acid
[2] Inhibitory activity on testosterone 5α-reductase in rats:
Test Methods
i) Materials
1,2,6,7-$^3$H-Testosterone (85–105 Ci/mmol):
  1,2,6,7-$^3$H-testosterone (85–105 Ci/mmol) is a mixture of 1,2,6,7-3H-testosterone and testosterone which includes 85–105 Ci of 1,2,6,7-$^3$H-testosterone per mmol of testosterone and is purchased from New England Nuclear, Boston, Mass., U.S.A.
Aquazol-2 (Aquazol-2 Universal LSC Cocktail)
  trademark, purchased from New England Nuclear, Boston, Mass., U.S.A.
ii) Preparation of prostatic testosterone 5α-reductase
Mature Spraque-Dawley male rats (7–8 weeks old) were sacrificed by diethyl ether. The ventral prostates were dissected to be free of their capsules and their combined volume was measured by displacement in several milliliters of ice-cold medium A (0.32M sucrose, 0.1 mM dithiothreitol and 20 mM sodium phosphate, pH 6.5). Unless specified, all the following procedures were carried out at 0 –4. The prostates were drained, minced, and then homogenized in 3 –4 tissue volumes of medium A with Pyrex-glass homogenizer. The homogenate was fractioned by differential centrifugations at 3,000 g for 15 minutes. The resulting pellets were resuspended in medium A. The suspension (20 –30 mg protein/ml) was stored at −80° C.
iii) Testosterone 5α-reductase assay The reaction solution contains 1 mM dithiothreitol, 40 mM sodium phosphate pH 6.5, 50 μM NADPH, 1,2,6,7-$^3$H-testosterone/testosterone ($2.2 \times 10^{-9}$M) and the suspension prepared above (0.8 g of protein) in a total volume of 565 μl. Test Compound was added to 10 μl of 10% ethanol, whereas control tubes received the same volume of 10% ethanol. The reaction was started with the addition of the enzyme suspension. After incubation at 37° C. for 30 minutes, the reaction mixture was extracted with 1 ml of ethyl acetate. Fifty 91 of ethyl acetate phase was chromatographed on a Merck silica plastic sheet Kieselgel 60 $F_{2\,5\,4}$, using ethyl acetate: cyclohexane (1:1) as the developing solvent system. The plastic sheet was air-dried and the testosterone and the 5α-dihydrotestosterone areas were cut off. The radioactivity was determined in 5 ml of Aquazol-2 in Packard scintillation counter (PACKARD TRI-CARB 4530), and an inhibitory ratio was calculated.

| [3] Test Result: | |
|---|---|
| Compound | $IC_{50}$ (M) |
| (1) | $4.4 \times 10^{-10}$ |

For therapeutic or preventive administration, the object compound (I) of the present invention which is suitable for oral, parenteral and external administration is used in the form of a conventional pharmaceutical preparation which contains said compound as an active ingredient, in admixture with pharmaceutically acceptable, substantially non-toxic carriers such as organic or inorganic solids and liquid excipients. The pharmaceutical preparation may be in a solid form such as tablet, granule, powder or capsule, or a liquid form such as solution, suspension, syrup, emulsion, lemonade or lotion.

If needed, there may be included in the above preparations auxiliary substances, stabilizing agents, wetting agents and other commonly used additives such as lactose, citric acid, tartaric acid, stearic acid, magnesium stearate, terra alba, sucrose, corn starch, talc, gelatin, agar, pectin, peanut oil, olive oil, cacao butter, and ethylene glycol.

While the dosage of the compound (I) may vary depending upon age and conditions of patients, the kind of diseases or conditions, the kind of the compound (I) to be used, etc. In general, amounts between about 0.01 mg and about 500 mg or even more per day may be administered to patients. An average single dose of about 0.05 mg, 0.1 mg, 0.25 mg, 0.5 mg, 1 mg, 20 mg, 50 mg, 100 mg of the object compound (I) of the present invention may be used for treating the diseases.

The following Preparation Examples and Examples are given for the purpose of illustrating the present invention.

Preparation Example 1

Heptanoyl chloride was added to a suspension of aluminum chloride in dichloromethane. The mixture was stirred at room temperature for 30 minutes. To the mixture was added a solution of indole in dichloromethane. The mixture was stirred at room temperature for 1 hour and poured into a mixture of hydrochloric acid and ethyl acetate. The organic layer was washed with water, dried over magnesium sulfate and evaporated. The residue was crystallized from diisopropyl ether to give 3-heptanoylindole as a white powder.

NMR (CDCl$_3$ +CD$_3$OD) δ: 8.36 (1H, m), 7.88 (1H, s), 7.42 (1H, m), 7.28 (2H, m), 2.88 (2H, t, J=7 Hz), 1.80 (2H, m), 1.2–1.5 (6H, m), 0.90 (3H, m)

Preparation Example 2

The procedure of Pre. Ex. 1 was repeated except that octanoyl chloride was used in place of heptanoyl chloride to give 3-octanoylindole.

NMR (CDCl$_3$ +CD$_3$OD) δ: 8.38 (1H, m), 7.88 (1H, s), 7.42 (1H, m), 7.28 (2H, m), 2.88 (2H, t, J=7 Hz), 1.80 (2H, m), 1.2–1.5 (8H, m), 0.90 (3H, m)

Preparation Example 3

The procedure of Pre. Ex. 1 was repeated except that nonanoyl chloride was used in place of heptanoyl chloride to give 3-nonanoylindole.

NMR (CDCl$_3$+CD$_3$OD) δ: 8.38 (1H, m), 7.88 (1H, s), 7.42 (1H, m), 7.28 (2H, m), 2.88 (2H, t, J=7 Hz), 1.80 (2H, m), 1.2–1.5 (10H, m), 0.90 (3H, m)

Preparation Example 4

The procedure of Pre. Ex. 1 was repeated except that decanoyl chloride was used in place of heptanoyl chloride to give 3-decanoylindole.

NMR (CDCl$_3$) δ: 8.86 (1H, br.s), 8.42 (1H, m), 7.88 (1H, d, J=2 Hz), 7.42 (1H, m), 7.30 (2H, m), 2.87 (2H, t, J=7 Hz), 1.80 (2H, m), 1.2–1.5 (12H, m), 0.87 (3H, m)

Preparation Example 5

The procedure of Pre. Ex. 1 was repeated except that undecanoyl chloride was used in place of heptanoyl chloride to give 3-undecanoylindole.

NMR (CDCl$_3$ +CD$_3$OD) δ: 8.38 (1H, m), 7.88 (1H, s), 7.42 (1H, m), 7.28 (2H, m), 2.85 (2H, t, J=7 Hz), 1.80 (2H, m), 1.2–1.5 (14H, m), 0.90 (3H, m)

Preparation Example 6

The procedure of Pre. Ex. 1 was repeated except that dodecanoyl chloride was used in place of heptanoyl chloride to give 3-dodecanoylindole.

NMR (CDCl$_3$+CD$_3$OD) δ: 8.38 (1H, m), 7.88 (1H, s), 7.42 (1H, m), 7.28 (2H, m), 2.85 (2H, t, J=7 Hz), 1.78 (2H, m), 1.2–1.5 (16H, m), 0.90 (3H, m)

Preparation Example 7

The procedure of Pre. Ex. 1 was repeated except that tridecanoyl chloride was used in place of heptanoyl chloride to give 3-tridecanoylindole.

NMR (CDCl$_3$+CD$_3$OD) δ: 8.38 (1H, m), 7.88 (1H, s), 7.42 (1H, m), 7.28 (2H, m), 2.85 (2H, t, J=7 Hz), 1.78 (2H, m), 1.2–1.5 (18H, m), 0.90 (3H, m)

Preparation Example 8

Step 1: Preparation of benzyl 6-bromohexyl ether

To a suspension of sodium hydride in 1,4-dioxane was added benzyl alcohol in 1,4-dioxane over a period of 30 minutes at 80° C., and the mixture was stirred for 1 hour. The obtained alkoxide solution was added to a solution of 1,6-dibromohexane in 1,4-dioxane at room temperature. The mixture was stirred at 80° C. for 14 hours and insoluble materials were filtered off. The filtrate was concentrated and the residue was distilled under reduced pressure to give the object compound.

$^1$H-NMR (CDCl$_3$, 200 MHz) δ: 7.2–7.4 (5H, m), 4.50 (2H, s), 3.48 (2H, t, J=7 Hz), 3.41 (2H, t, J=7 Hz), 1.87 (2H, m), 1.3–1.75 (6H, m)

Step 2: Preparation of 10-benzyloxy-4-(4-isobutylphenyl)-4decanol

A solution of 6-benzyloxyhexylmagnesium bromide was prepared from benzyl 6-bromohexyl ether, magnesium and tetrahydrofuran in a usual manner. To the obtained Grinard solution was added dropwise a solution of 4'-isobutylbutyrophenone in tetrahydrofuran dropwise over a period of 30 minutes at room temperature, and the mixture was stirred for 15 minutes. Aqueous ammonium chloride was added to the reaction mixture, and then extracted with ethyl acetate. The organic layer was washed with water and brine, dried over magnesium sulfate, and concentrated. The residue was chromatographed on a silica gel column to give the object compound.

$^1$H-NMR (CDCl$_3$, 200 MHz) δ: 7.2–7.4 (7H, m), 7.09 (2H, d, J=9 Hz), 4.48 (2H, s), 3.41 (2H, t, J=7 Hz), 2.46 (2H, d, J=7 Hz), 0.8–2.0 (25H, m)

Step 3: Preparation of 7-(4-isobutylphenyl)-1-decanol

A mixture of 10-benzyloxy-4-(4-isobutylphenyl)-4-decanol and p-toluenesulfonic acid in benzene was refluxed for 20 minutes. The mixture was diluted with ethyl acetate, washed with water and brine, dried over magnesium sulfate and concentrated.

The residue was dissolved in a mixture of methanol and 1,4dioxane, and then 10% palladium-carbon was added to the solution, followed by agitation of the mixture in a hydrogen atmosphere at room temperature for 3 hours. Removal of catalyst and evaporation of the solvent gave the object compound as an oil.

$^1$H-NMR (CDCl$_3$, 200 MHz) δ: 6.95–7.1 (4H, m), 3.60 (2H, t, J=7 Hz), 2.35–2.55 (3H, m), 1.85 (1H, m), 1.0–1.7 (15H, m), 0.75–0.95 (9H, m)

Step 4: Preparation of 1-bromo-7-(4-isobutylphenyl)decane

To a mixture of 7-(4-isobutylphenyl)-1-decanol and carbon tetrabromide in tetrahydrofuran was added portionwise triphenylphosphine. The mixture was stirred at room temperature for 2 hours and insoluble materials were filtered off. The filtrate was concentrated and n-hexane was added thereto, then the mixture was filtered again and the filtrate was concentrated. The residue was chromatographed on a silica gel column (n-hexane as eluent) to give the object compound as an oil.

$^1$H-NMR (CDCl$_3$, 200 MHz) δ: 7.03 (4H, m), 3.37 (2H, t, J=7 Hz), 2.35–2.55 (3H, m), 1.05–1.95 (15H, m), 0.8–0.95 (9H, m)

Step 5: Preparation of 8-(4-isobutylphenyl)undecanoic acid

A solution of 7-(4-isobutylphenyl)decylmagnesium bromide was prepared from magnesium, 1-bromo-7-(4-isobutylphenyl)decane and tetrahydrofuran in a usual manner. Dry ice was added to the obtained. Grinard solution, and the mixture was stirred for 10 minutes. The mixture was poured into diluted hydrochloric acid and extracted with ethyl acetate. The organic phase was washed with water and brine, dried over magnesium sulfate and concentrated. The residue was chromatographed on a silica gel column to give the object compound as an oil.

¹H-NMR (CDCl₃, 200 MHz) δ: 6.95–7.1 (4H, m), 2.35–2.55 (3H, m), 2.30 (2H, t, J=7.5 Hz), 1.85 (1H, m), 1.05–1.7 (14H, m), 0.8–0.95 (9H, m)

Step 6: Preparation of 3-[8-(4-isobutylphenyl)undecanoyl]indole

To a solution of 8-(4-isobutylphenylphenyl)undecanoic acid in dichloromethane was added oxalyl chloride and a catalytic amount of N,N-dimethylformamide at room temperature. After the mixture was stirred for 1 hour, it was concentrated. The residue was dissolved in dichloromethane, and then aluminum chloride was added thereto at 0° C. After stirring for 30 minutes, a solution of indole in dichloromethane was added. After being stirred for 1 hour at room temperature, the mixture was poured into ice water and extracted with dichloromethane. The organic layer was washed with diluted hydrochloric acid, water and brine, dried over magnesium sulfate and concentrated. The residue was chromatographed on a silica gel column to give the object compound.

¹H-NMR (CDCl₃, 200 MHz) δ: 8.57 (1H, br.s), 8.40 (1H, m), 7.83 (1H, d, J=3.5 Hz), 7.25–7.45 (3H, m), 6.95–7.1 (4H, m), 2.83 (2H, t, J=7.5 Hz), 2.35–2.45 (3H, m), 1.0–1.95 (15H, m), 0.75–0.95 (9H, m)

Preparation Example 9

Step 1: Preparation of 6-(4-isobutylphenyl)-1-decanol

The procedure of Steps 1–3 of Pre. Ex. 8 was repeated except that 1,5-dibromopentane was used as a starting compound in place of 1,6-dibromohexane to give the object compound.

¹H-NMR (CDCl₃, 200 MHz) δ: 6.95–7.1 (4H, m), 3.58 (2H, t, J=7 Hz), 2.35–2.55 (3H, m), 1.85 (1H, m), 1.0–1.75 (14H, m), 0.75–0.95 (9H, m)

Step 2: Preparation of 6-(4-isobutylphenyl)decanoic acid

Chromium(VI) oxide was dissolved in an aqueous solution of sulfuric acid, and diluted with water to give a Jones reagent.

To a solution of 6-(4-isobutylphenyl)-1-decanol in acetone was added the obtained Jones reagent until an orange-brown color persisted. After the mixture was stirred at room temperature for 1 hour, 2-propanol was added thereto. The resultant mixture was diluted with ethyl acetate and washed with water and brine, dried over magnesium sulfate and concentrated. Flash chromatography on a silica gel column (hexane-ethyl acetate, 2:1) afforded the object compound as an oil.

¹H-NMR (CDCl₃, 200 MHz) δ: 6.95–7.1 (4H, m), 2.35–2.55 (3H, m), 2.28 (2H, t, J=7.5 Hz), 1.84 (1H, m), 1.4–1.7 (6H, m), 1.0–1.35 (6H, m), 0.75–0.95 (9H, m)

Step 3: Preparation of 3-[6-(4-isobutylphenyl)decanoyl]indole

To a solution of the obtained 6-(4-isobutylphenyl)decanoic acid in dichloromethane was added oxalyl chloride and a catalytic amount of N,N-dimethylformamide. After the mixture was stirred at room temperature for 30 minutes, the solvent was evaporated to give a corresponding acid chloride.

To a solution of methylmagnesium bromide in diethyl ether was added a solution of indole in diethyl ether at room temperature. After the mixture was stirred for 20 minutes, a solution of the acid chloride obtained above in diethyl ether was added rapidly. The reaction mixture was stirred at room temperature for 30 minutes, then a saturated aqueous solution of ammonium chloride was added and the mixture was extracted with ethyl acetate. The organic layer was washed with water, aqueous sodium bicarbonate and brine, dried and concentrated. Flash chromatography on a silica gel column afforded the object compound.

¹H-NMR (DMSO-d₆, 200 MHz) δ: 8.32 (1H, s), 8.28 (1H, s), 8.17 (1H, m), 7.45 (1H, m), 6.95–7.25 (6H, m), 2.77 (2H, t, J=7.5 Hz), 2.3–2.5 (3H, m), 1.35–1.9 (7H, m), 0.95–1.3 (6H, m), 0.7–0.9 (9H, m)

Preparation Example 10

Step 1: Preparation of 7-(4-isobutylphenyl)decanoic acid

The procedure of Steps 4–5 of Pre. Ex. 8 was repeated except that 6-(4-isobutylphenyl)-1-decanol was used in place of 7-(4-isobutylphenyl)-1-decanol to give the object compound.

¹H-NMR (CDCl₃, 200 MHz) δ: 6.95–7.1 (4H, m), 2.35–2.5 (3H, m), 2.28 (2H, t, J=7.5 Hz), 1.85 (1H, m), 1.0–1.7 (14H, m), 0.75–0.95 (9H, m)

Step 2: Preparation of 3-[7-(4-isobutylphenyl)undecanoyl]indole

To a solution of the obtained 7-(4-isobutylphenyl)undecanoic acid in dichloromethane was added oxalyl chloride and a catalytic amount of N,N-dimethylformamide. After the mixture was stirred at room temperature for 1 hour, the solvent was evaporated to give a corresponding acid chloride.

To a solution of methylmagnesium bromide in diethyl ether was added a solution of indole in diethyl ether at room temperature. After 15 minutes, zinc chloride in diethyl ether was added thereto. The mixture was stirred at room temperature for 30 minutes, and then the acid chloride obtained above in diethyl ether was added rapidly. The reaction mixture was stirred for 15 minutes, added with saturated aqueous ammonium chloride and extracted with ethyl acetate. The organic layer was washed with water, aqueous sodium bicarbonate and brine, dried and concentrated. Flash chromatography on a silica gel column afforded the object compound.

¹H-NMR (CDCl₃, 200 MHz) δ: 8.66 (1H, br.s), 8.39 (1H, m), 7.80 (1H, d, J=3 Hz), 7.25–7.45 (3H, m), 6.95–7.1 (4H, m), 2.79 (2H, t, J=7.5 Hz), 2.35–2.5 (3H, m), 1.0–1.95 (14H, m), 0.75–0.95 (9H, m)

Preparation Example 11

Step 1: Preparation of 6-butyl-1-decanol

The procedure of Steps 2-3 of Pre. Ex. 8 was repeated except that benzyl 5-bromopentyl ether was used in place of benzyl 6-bromohexyl ether to give the object compound.

¹H-NMR (CDCl₃, 200 MHz) δ: 3.65 (2H, t, J=7 Hz), 1.5–1.7 (3H, m), 1.1–1.4 (19H, m), 0.89 (6H, t, J=6.5 Hz)

Step 2: Preparation of 6-butyldecanoic acid

The procedure of Step 2 of Pre. Ex. 9 was repeated except that 6-butyl-1-decanol was used in place of 6-(4-isobutylphenyl)-1-decanol to give the object compound.

¹H-NMR (CDCl₃, 200 MHz) δ: 2.37 (2H, t, J=7.5 Hz), 1.5–1.7 (2H, m), 1.1–1.4 (17H, m), 0.89 (6H, t, J=6.5 Hz)

Step 3: Preparation of 3-(6-butyldecanoyl)indole

The procedure of Step 2 of Pre. Ex. 10 was repeated except that 6-butyldecanoic acid was used in place of 7-(4-isobutylphenyl)undecanoic acid to give the object compound.

¹H-NMR (CDCl₃, 200 MHz) δ: 8.73 (1H, br.s), 8.41 (1H, m), 7.89 (1H, d, J=3 Hz), 7.15–7.45 (3H, m), 2.88 (2H, t, J=7.5 Hz), 1.78 (2H, m), 1.1–1.5 (17H, m), 0.88 (6H, t, J=6.5 Hz)

Preparation Example 12

Step 1: Preparation of 5-(4-isobutylphenyl)valeric acid

To a suspension of 3-ethoxycarbonylpropyltriphenylphosphonium bromide in tetrahydrofuran was added potassium t-butoxide at room temperature. After the mixture was stirred for 1 hour, 4-isobutylbenzaldehyde was added and the mixture was stirred at room temperature for 1 hour. After filtration, the obtained organic solution was concentrated and diluted with ethyl acetate, washed with water and brine and dried over magnesium sulfate. Evaporation of the solvent followed by flash chromatography on silica gel column gave an oil.

A mixture of the obtained oil and a in solution of sodium hydroxide in ethanol and 1,4-dioxane was stirred at room temperature for 2 hours. The mixture was acidified with diluted hydrochloric acid, and extracted with ethyl acetate. The organic solution was washed with water and brine, dried and concentrated. The residue was dissolved in methanol and then 10% palladium-carbon was added and the mixture was stirred in a hydrogen atmosphere at room temperature for 1 hour. Removal of catalyst and evaporation of the solvent afforded the object compound.

$^1$H-NMR (CDCl$_3$, 200 MHz) δ: 7.0–7.15 (4H, m), 2.60 (2H, t, J=7 Hz), 2.3–2.5 (4H, m), 1.84 (1H, m), 1.6–1.75 (4H, m), 0.89 (6H, d, J=7 Hz)

Step 2: Preparation of 3-[5-(4-isobutylphenyl)valeryl]indole

The procedure of Step 2 of Pre. Ex. 10 was repeated except that 5-(4-isobutylphenyl)valeric acid was used in place of 7-(4isobutylphenyl)undecanoic acid to give the object compound.

$^1$H-NMR (CDCl$_3$, 200 MHz) δ: 8.63 (1H, br.s), 8.40 (1H, m), 7.82 (1H, d, J=3 Hz), 7.2–7.45 (3H, m), 6.95–7.15 (4H, m), 2.88 (2H, t, J=7 Hz), 2.62 (2H, t, J=7 Hz), 2.42 (2H, d, J=7 Hz), 1.45–1.95 (5H, m), 0.88 (6H, d, J=7 Hz)

Preparation Example 13

The procedure of Step 2 of Pre. Ex. 10 was repeated except that 4-methylvaleric acid was used in place of 7-(4-isobutylphenyl)undecanoic acid to give 3-(4-methylvaleryl)indole.

$^1$H-NMR (DMSO-d$_6$, 200 MHz) δ: 8.33 (1H, s), 8.19 (1H, m), 7.46 (1H, m), 7.19 (2H, m), 2.83 (2H, t, J=7.5 Hz), 1.45–1.75 (3H, m), 0.91 (6H, d, J=6.5 Hz)

Preparation Example 14

The procedure of Step 2 of Pre. Ex. 10 was repeated except that 3-linoleic acid was used in place of 7-(4-isobutylphenyl)undecanoic acid to give 3-linoleylindole.

$^1$H-NMR (CDCl$_3$, 200 MHz) δ: 8.60 (1H, br.s), 7.88 (1H, d, J=3 Hz), 7.41 (1H, m), 7.2–7.45 (3H, m), 5.25–5.45 (4H, m), 2.88 (2H, t, J=7.5 Hz), 2.78 (2H, t, J=6 Hz), 1.95–2.15 (4H, m), 1.79 (2H, m), 1.2–1.5 (14H, m), 0.88 (3H, t, J=7 Hz)

Preparation Example 15

The procedure of Step 2 of Pre. Ex. 10 was repeated except that 3,7-dimethyl-6-octenoic acid was used in place of 7-(4-isobutylphenyl)undecanoic acid and ethylmagnesium bromide was used in place of methylmagnesium bromide to give 3-(3,7-dimethyl-6-octenoyl)indole.

$^1$H-NMR (CDCl$_3$, 200 MHz) δ: 8.72 (1H, br.s), 8.44 (1H, m), 7.85 (1H, d, J=3 Hz), 7.2–7.45 (3H, m), 5.10 (1H, t, J=7 Hz), 2.6–2.9 (2H, m), 1.9–2.35 (3H, m), 1.15–1.8 (8H, m), 0.99 (3H, d, J=7 Hz)

Preparation Example 16

The procedure of Pre. Ex. 15 was repeated except that trans-4-pentylcyclohexanecarboxylic acid was used in place of 3,7-dimethyl-6-octenoic acid to give trans-3-(4-pentylcyclohexylcarbonyl)indole.

$^1$H-NMR (DMSO-d$_6$, 200 MHz) δ: 8.35 (1H, s), 8.18 (1H, m), 7.45 (1H, m), 7.05–7.25 (2H, m), 3.13 (1H, m), 0.75–1.9 (20H, m)

Preparation Example 17

Step 1: Preparation of 4'-isobutylvalerophenone

A mixture of valeryl chloride and aluminium chloride in dichloromethane was stirred at 0° C. for 30 minutes, and then isobutylbenzene was added. After stirring at 0° C. for 1 hour, the mixture was poured into ice water and extracted with dichloromethane. The organic layer was washed with an aqueous solution of sodium bicarbonate and brine, dried over magnesium sulfate and concentrated to give the object compound.

$^1$H-NMR (CDCl$_3$, 200 MHz) δ: 7.88 (2H, d, J=8.5 Hz), 7.22 (2H, d, J=8.5 Hz), 2.95 (2H, t, J=7 Hz), 2.53 (2H, d, J=7 Hz), 1.6–2.0 (3H, m), 1.3–1.5 (2H, m), 0.85–1.0 (9H, m)

Step 2: Preparation of 1-(4-isobutylphenyl)pentanol

To a solution of 4'-isobutylvalerophenone in 2-propanol was added sodium borohydride, and the mixture was stirred at 50° C. for 5 hours. The reaction mixture was poured into ice water, acidified with 6N hydrochloric acid and extracted with ethyl acetate. The organic layer was washed with water and brine, dried over magnesium sulfate and concentrated to give the object compound.

$^1$H-NMR (CDCl$_3$, 200 MHz) δ: 7.25 (2H, d, J=8.5 Hz), 7.12 (2H, d, J=8.5 Hz), 4.63 (1H, t, J=7 Hz), 2.47 (2H, d, J=7 Hz), 1.6–1.95 (3H, m), 1.15–1.5 (4H, m), 0.8–0.95 (9H, m)

Step 3: Preparation of 3-[1-(4-isobutylphenyl)pentyloxy]propanol

To a mixture of 1-(4-isobutylphenyl)pentanol and carbon tetrabromide in tetrahydrofuran was added triphenylphosphine and the mixture was stirred at room temperature for 1 hour. Insoluble materials were removed by filtration and the filtrate was concentrated. Hexane was added to the residue and the mixture was filtered again. Concentration of the filtrate gave crude 1-bromo-1-(4-isobutylphenyl)pentane. Sodium was added portionwise to 1,3-propanediol at 80° C. while stirring. The obtained crude 1-bromo-1-(4-isobutylphenyl)pentane was added thereto, and the mixture was stirred at 120° C. for 30 minutes. After the mixture was cooled, diluted hydrochloric acid was added thereto, and the mixture was extracted with ethyl acetate.

The organic layer was washed with water and brine, dried over magnesium sulfate and concentrated. Silica gel column chromatography of the concentrate afforded the object compound.

$^1$H-NMR (CDCl$_3$, 200 MHz) δ: 7.05–7.2 (4H, m), 4.15 (1H, t, J=7 Hz), 3.77 (2H, m), 3.46 (2H, m), 2.48 (1H, t, J=5.5 Hz), 2.47 (2H, d, J=7 Hz), 1.5–2.0 (5H, m), 1.1–1.45 (4H, m), 0.8–0.95 (9H, m)

Step 4: Preparation of 3-[1-(4-isobutylphenyl)pentyloxy]propionic acid

Chromium(VI) oxide was dissolved in an aqueous solution of sulfuric acid, and diluted with water to give a Jones reagent. To a solution of 3-[1-(4-isobutylphenyl)pentyloxy]propanol in acetone was added the obtained Jones reagent at room temperature until an orange-brown color persisted. After 10 minutes, 2-propanol was added to the reaction mixture. Ethyl acetate was added thereto, and the mixture was washed with water and brine, dried over magnesium sulfate and concentrated. Silica gel column chromatography of the concentrate afforded the object compound.

$^1$H-NMR (CDCl$_3$, 200 MHz) δ: 7.05–7.2 (4H, m), 4.21 (1H, t, J=7 Hz), 3.55 (2H, m), 2.60 (2H, t, J=6 Hz), 2.48 (2H, d, J=7 Hz), 1.5–2.0 (3H, m), 1.1–1.45 (4H, m), 0.8–0.95 (9H, m)

Step 5: Preparation of 3-[3-[1-(4-isobutylphenyl)pentyloxy]propionyl]indole

The procedure of Pre. Ex. 15 was repeated except that 3-[1-(4-isobutylphenyl)pentyloxy]propionic acid was used in place of 3,7-dimethyl-6-octenoic acid to give the object compound.

$^1$H-NMR (CDCl$_3$, 200 MHz) δ: 8.63 (1H, br.s), 8.38 (1H, m), 7.85 (1H, d, J=3 Hz), 7.2–7.45 (3H, m), 7.18 (2H, d, J=8.5 Hz), 7.08 (2H, d, J=8.5 Hz), 4.21 (1H, t, J=7 Hz), 3.76 (2H, t, J=7 Hz), 2.95–3.3 (2H, m), 2.45 (2H, d, J=7 Hz), 1.5–1.95 (3H, m), 1.05–1.4 (4H, m), 0.75–0.95 (9H, m)

Preparation Example 18

The procedure of Steps 3 to 5 of Pre. Ex. 17 was repeated except that 1,5-pentanediol was used in place of 1,3-propanediol, and 1-(4-isobutylphenyl)pentanol was used in place of 1(4-isobutylphenyl)pentanol to give 3-[5-[1-(4-isobutylphenyl)-pentyloxy]valerylindole.

$^1$H-NMR (CDCl$_3$, 200 MHz) δ: 8.57 (1H, br.s), 8.40 (1H, m), 7.81 (1H, d, J=3 Hz), 7.0–7.45 (7H, m), 4.13 (1H, t, J=7 Hz), 3.15–3.5 (2H, m), 2.86 (2H, t, J=7 Hz), 2.46 (2H, d, J=7 Hz), 1.1–2.0 (11H, m), 0.75–0.95 (9H, m)

Preparation Example 19

Step 1: Preparation of 2-[1-(4-isobutylphenyl)pentyloxy]ethanol

To a mixture of 1-(4-isobutylphenyl)pentanol and carbon tetrabromide in tetrahydrofuran was added triphenylphosphine, and the mixture was stirred at room temperature for 30 minutes. Insoluble materials were removed by filtration and the filtrate was concentrated. Hexane was added to the residue and the mixture was filtered again. Concentration of the filtrate gave crude 1-bromo-1-(4-isobutylphenyl)pentane. Sodium was added portionwise to ethylene glycol at 80° C. while stirring. To the resultant solution was added the obtained crude 1-bromo-1-(4-isobutylphenyl)pentane, and the mixture was stirred at 120° C. for 1 hour. After the mixture was cooled, diluted hydrochloric acid was added, and the mixture was extracted with ethyl acetate. The organic layer was washed with water and brine, dried over magnesium sulfate and concentrated. Silica gel column chromatography of the concentrate afforded the object compound.

$^1$H-NMR (CDCl$_3$, 200 MHz) δ: 7.05–7.25 (4H, m), 4.20 (1H, t, J=7 Hz), 3.69 (2H, m), 3.40 (2H, m), 2.47 (2H, d, J=7 Hz), 1.1–2.05 (7H, m), 0.8–0.95 (9H, m)

Step 2: Preparation of (E)-ethyl 4-[1-(4-isobutylphenyl)pentyloxy]-2-butenoate

To a mixture of 2-[1-(4-isobutylphenyl)pentyloxy]ethanol and triethylamine in dimethylsulfoxide was added sulfur trioxide-pyridine complex at room temperature. After 30 minutes, the mixture was poured into ice water. The mixture was extracted with diethyl ether. The organic layer was washed with diluted hydrochloric acid and water, dried over magnesium sulfate and concentrated. The residue was dissolved in N,N-dimethylformamide, and triethyl phosphonoacetate was added thereto. Then, sodium hydride was added to the mixture at 0° C. After 1 hour, diluted hydrochloric acid was added to the reaction mixture, and the mixture was extracted with ethyl acetate. The organic layer was washed with water and brine, dried over magnesium sulfate and concentrated. Silica gel column chromatography of the concentrate afforded the object compound.

$^1$H-NMR (CDCl$_3$, 200 MHz) δ: 7.05–7.25 (4H, m), 6.93 (1H, dt, J=4 Hz, 16 Hz), 6.11 (1H, dt, J=1.5 Hz, 16 Hz), 4.21 (2H, q, J=7 Hz), 3.8–4.1 (2H, m), 2.47 (2H, d, J=7 Hz), 1.1–2.0 (10H, m), 0.8–0.95 (9n, m)

Step 3: Preparation of (E)-4-[1-(4-isobutylphenyl)pentyloxy]-2butenoic acid

To a solution of (E)-ethyl 4-[1-(4-isobutylphenyl)pentyloxy]-2-butenoate in ethanol and 1,4-dioxane was added a 4N aqueous solution of sodium hydroxide. After being stirred at 80° C. for 5 hours, the mixture was cooled, concentrated and acidified with diluted hydrochloric acid. The mixture was extracted with ethyl acetate, and the organic layer was washed with water and brine and dried over magnesium sulfate. Evaporation of the solvent and silica gel column chromatography of the residue afforded the object compound.

$^1$H-NMR (CDCl$_3$, 200 MHz) δ: 6.95–7.25 (5H, m), 6.12 (1H, dt, J=1.5 Hz, 16 Hz), 4.22 (1H, t, J=7 Hz), 3.85–4.15 (2H, m), 2.47 (2H, d, J=7 Hz), 1.1–2.0 (7H, m), 0.8–0.95 (9H, m)

Step 4: Preparation of (E)-3-[4-[1-(4-isobutylphenyl)pentyloxy]-2-butenoyl]indole The procedure of Pre. Ex. 15 was repeated except that (E)-4-[1-(4-isobutylphenyl)pentyloxy]-2-butenoic acid was used in place of 3,7-dimethyl-6-octenoic acid to give the object compound.

$^1$H-NMR (CDCl$_3$, 200 MHz) δ: 8.72 (1H, br.s), 8.48 (1H, m), 7.90 (1H, d, J=3 Hz), 7.0–7.45 (9H, m), 4.30 (1H, t, J=7 Hz), 3.95–4.25 (2H, m), 2.48 (2H, d, J=7 Hz), 1.15–2.0 (7H, m), 0.8–1.0 (9H, m)

Step 5: Preparation of 4-methoxybenzyl 4-bromobutyrate

To a solution of 4-methoxybenzyl alcohol and triethylamine in dichloromethane was added 4-bromobutyryl chloride at 0° C. The mixture was stirred at 0° C. for 30 minutes, and the solvent was evaporated. The residue was diluted with ethyl acetate, and the organic solution was washed with water and brine, dried over magnesium sulfate and concentrated. The concentrate was chromatographed on a silica gel column to give the object compound.

$^1$H-NMR (CDCl$_3$, 200 MHz) δ: 7.30 (2H, d, J=9 Hz), 6.90 (2H, d, J=9 Hz), 5.07 (2H, s), 3.81 (3H, s), 3.47 (2H, t, J=7 Hz), 2.53 (2H, t, J=7 Hz), 2.18 (2H, m)

Preparation Example 20

A mixture of ethyl succinyl chloride and aluminium chloride in dichloromethane was stirred at room temperature for 20 minutes, and then a solution of indole in dichloromethane was added. After being stirred at room temperature for 1 hour, the mixture was poured into ice water, and the mixture was extracted with dichloromethane. The organic layer was washed with an aqueous solution of sodium bicarbonate and brine, dried over magnesium sulfate and concentrated. The residue was chromatographed on a silica gel column to give 3-(3-ethoxycarbonylpropionyl)indole.

$^1$H-NMR (DMSO-d$_6$, 200 MHz) δ: 8.37 (1H, s), 8.16 (1H, m), 7.47 (1H, m), 7.19 (2H, m), 4.06 (2H, q, J=7 Hz), 3.18 (2H, t, J=7 Hz), 2.64 (2H, t, J=7 Hz), 1.19 (3H, t, J=7 Hz)

Preparation Example 21

Step 1: Preparation of 11-benzyloxycarbonylundecanoic acid

A mixture of 1,10-decanedicarboxylic acid, benzyl bromide and potassium carbonate in N,N-dimethylformamide was stirred at room temperature for 16 hours. The reaction mixture was poured into a mixture of ethyl acetate and diluted hydrochloric acid, and the organic layer was washed with water and brine, dried over magnesium sulfate and concentrated. The residue was chromatographed on a silica gel column to give the object compound.

$^1$H-NMR (CDCl$_3$, 200 MHz) δ: 7.25–7.45 (5H, m), 5.12 (2H, s), 2.36 (4H, t, J=7 Hz), 1.5–1.75 (4H, m), 1.15–1.45 (12H, m)

Step 2: Preparation of 3-(11-benzyloxycarbonylundecanoyl)indole

The procedure of Pre. Ex. 15 was repeated except that 11-benzyloxycarbonylundecanoic acid was used in place of 3,7-dimethyl-6-octenoic acid to give the object compound.

$^1$H-NMR (CDCl$_3$, 200 MHz) δ: 8.78 (1H, br.s), 8.41 (1H, m), 7.87 (1H, d, J=3 Hz), 7.2–7.45 (8H, m), 5.12 (2H, s), 2.86 (2H, t, J=7 Hz), 2.35 (2H, t, J=7 Hz), 1.55–1.85 (4H, m), 1.15–1.5 (12H, m)

Preparation Example 22

Step 1: Preparation of (E)-ethyl 2-nonenoate

To a mixture of triethyl phosphonoacetate and heptaldehyde in N,N-dimethylformamide was added sodium hydride at 0° C. while stirring. After 1 hour, diluted hydrochloric acid was added to the reaction mixture, and the mixture was extracted with ethyl acetate. The organic layer was washed with water and brine, dried over magnesium sulfate and concentrated. Silica gel column chromatography of the concentrate afforded the object compound.

$^1$H-NMR (CDCl$_3$, 200 MHz) δ: 6.98 (1H, dt, J=7 Hz, 16 Hz), 5.80 (1H, dt, J=1.5 Hz, 16 Hz), 4.18 (2H, q, J=7 Hz), 2.19 (2H, m), 1.2–1.55 (11H, m), 0.89 (3H, t, J=7 Hz)

Step 2: Preparation of (E)-2-nonenoic acid

To a solution of (E)-ethyl 2-nonenoate in ethanol and 1,4-dioxane was added a 1N aqueous solution of sodium hydroxide. After being stirred at room temperature for 3 hours, the reaction mixture was concentrated and acidified with diluted hydrochloric acid, and the mixture was extracted with ethyl acetate. The organic layer was washed with water and brine, dried over magnesium sulfate and concentrated to give the object compound.

$^1$H-NMR (CDCl$_3$, 200 MHz) δ: 7.09 (1H, dt, J=7 Hz, 16 Hz), 5.82 (1H, dt, J=1.5 Hz, 16 Hz), 2.23 (2H, m), 1.15–1.65 (8H, m), 0.8–1.0 (3H, t, J=7 Hz)

Step 3: Preparation of (E)-3-(2-nonenoyl)indole The procedure of Pre. Ex. 15 was repeated except that (E)- 2-nonenoic acid was used in place of 3,7-dimethyl-6-octenoic acid to give the object compound.

$^1$H-NMR (CDCl$_3$, 200 MHz) δ: 8.92 (1H, br.s), 8.49 (1H, m), 7.91 (1H, d, J=3 Hz), 7.25–7.4 (3H, m), 7.08 (1H, dt, J=7 Hz, 16 Hz), 6.78 (1H, d, J=16 Hz), 2.30 (2H, q, J=7 Hz), 1.15–1.7 (8H, m), 0.90 (3H, t, J=7 Hz)

Preparation Example 23

The procedure of Pre. Ex. 22 (Steps 1–3) was repeated except that octyl aldehyde was used in place of heptaldehyde to give (E)-3-(2-decenoyl)indole.

$^1$H-NMR (CDCl$_3$, 200 MHz) δ: 8.91 (1H, br.s), 8.48 (1H, m), 7.90 (1H, d, J=3 Hz), 7.2–7.5 (3H, m), 7.08 (1H, dt, J=7 Hz, 16 Hz), 6.77 (1H, dt, J=1.5 Hz, 16 Hz), 2.30 (2H, m), 1.15–1.65 (10H, m), 0.89 (3H, t, J=7 Hz)

Preparation Example 24

The procedure of Pre. Ex. 22 was repeated except that triethyl phosphonoacetate was used in place of triethyl phosphonoacetate, and nonyl aldehyde was used in place of heptaldehyde to give (E)-3-(2-undecenoyl)indole.

$^1$H-NMR (CDCl$_3$, 200 MHz) δ: 8.90 (1H, br.s), 8.48 (1H, m), 7.90 (1H, d, J=3 Hz), 7.2–7.5 (3H, m), 7.08 (1H, dt, J=7 Hz, 16 Hz), 6.78 (1H, dt, J=1.5 Hz, 16 Hz), 2.30 (2H, m), 1.15–1.65 (12H, m), 0.89 (3H, t, J=7 Hz)

Preparation Example 25

The procedure of Pre. Ex. 22 was repeated except that triethyl 2-phosphonopropionate was used in place of triethyl phosphonoacetate, and nonyl aldehyde was used in place of heptaldehyde to give (E)-3-(2-methyl-2-undecenoyl)indole.

$^1$H-NMR (CDCl$_3$, 200 MHz) δ: 8.75 (1H, br.s), 8.32 (1H, m), 7.64 (1H, d, J=3 Hz), 7.2–7.5 (3H, m), 6.35 (1H, dt, J=1 Hz, 7 Hz), 2.27 (2H, q, J=7 Hz), 2.00 (3H, d, J=1 Hz), 1.15–1.6 (12H, m), 0.88 (3H, t, J=7 Hz)

Preparation Example 26

The procedure of Pre. Ex. 22 was repeated except that 8-heptadecanone was used in place of heptaldehyde to give 3-(3-heptyl-2-decenoyl)indole.

$^1$H-NMR (CDCl$_3$, 200 MHz) δ: 8.64 (1H, br.s), 8.47 (1H, m), 7.85 (1H, d, J=3 Hz), 7.2–7.45 (3H, m), 6.58 (1H, s), 2.67 (2H, t, J=7 Hz), 2.23 (2H, t, J=7 Hz), 1.15–1.65 (20H, m), 0.8–1.0 (6H, m)

Preparation Example 27

The procedure of Pre. Ex. 22 was repeated except that 4-isobutylbenzaldehyde was used in place of heptaldehyde to give (E)-3-(4-isobutylcinnamoyl)indole.

$^1$H-NMR (CDCl$_3$, 200 MHz) δ: 8.93 (1H, br.s), 8.53 (1H, m), 8.02 (1H, d, J=3 Hz), 7.83 (1H, d, J=16 Hz), 7.56 (2H, d, J=8.5 Hz), 7.25–7.5 (4H, m), 7.19 (2H, d, J=8.5 Hz), 2.51 (2H, d, J=7 Hz), 1.90 (1H, m), 0.92 (6H, d, J=7 Hz)

Preparation Example 28

The procedure of Pre. Ex. 15 was repeated except that 4-methoxycinnamic acid was used in place of 3,7-dimethyl-6-octenoic acid to give (E)-3-(4-methoxycinnamoyl)indole.

$^1$H-NMR (DMSO-d$_6$, 200 MHz) δ: 8.72 (1H, d, J=3 Hz), 8.33 (1H, m), 7.45–7.9 (5H, m), 7.15–7.35 (2H, m), 7.02 (2H, d, J=8.5 Hz), 3.82 (3H, s)

Preparation Example 29

The procedure of Pre. Ex. 15 was repeated except that cinnamic acid was used in place of 3,7-dimethyl-6-octenoic acid to give (E)-3-cinnamoylindole.

$^1$H-NMR (DMSO-d$_6$, 200 MHz) δ: 8.75 (1H, d, J=3 Hz), 8.34 (1H, m), 7.8–7.95 (3H, m), 7.63 (1H, d, J=16 Hz), 7.4–7.55 (4H, m), 7.15–7.35 (2H, m)

Preparation Example 30

A mixture of indole-3-carboxylic acid, 1-bromononane and potassium carbonate in N,N-dimethylformamide was stirred at room temperature for 15 hours. After insoluble materials were filtered off, the filtrate was diluted with ethyl acetate, washed with water and brine, dried over magnesium sulfate and concentrated. The solid was collected and washed with hexane to give nonyl indole-3-carboxylate.

$^1$H-NMR (CDCl$_3$, 200 MHz) δ: 8.63 (1H, br.s), 8.18 (1H, m), 7.93 (1H, d, J=3 Hz), 7.2–7.5 (3H, m), 4.34 (2H, t, J=7 Hz), 1.15–1.9 (14H, m), 0.88 (3H, t, J=7 Hz)

Preparation Example 31

Step 1: Preparation of benzyl indole-3-carboxylate

The procedure of Pre. Ex. 30 was repeated except that benzyl bromide was used in place of 1-bromononane to give the object compound.

$^1$H-NMR (DMSO-$d_6$, 200 MHz) δ: 8.16 (1H, s), 7.98 (1H, m), 7.1–7.55 (8H, m), 5.34 (2H, s)

Step 2: Preparation of ethyl 4-(3-benzyloxycarbonyl-1-indolyl)-butyrate

A mixture of benzyl indole-3-carboxylate, ethyl 4-bromobutyrate and potassium t-butoxide in N,N-dimethylformamide was stirred at 50° C. for 4 hours. After insoluble materials were filtered off, the filtrate was diluted with ethyl acetate, and washed with diluted hydrochloric acid and water, dried over magnesium sulfate and concentrated. The concentrate was chromatographed on a silica gel column to give the object compound.

$^1$H-NMR (CDCl$_3$, 200 MHz) δ: 8.19 (1H, m), 7.85 (1H, s), 7.2–7.5 (8H, m), 5.39 (2H, s), 4.25 (2H, t, J=7 Hz), 4.13 (2H, q, J=7 Hz), 2.1–2.35 (4H, m), 1.25 (3H, t, J=7 Hz)

Step 3: Preparation of 1-(3-ethoxycarbonylpropyl)indole-3-carboxylic acid

A mixture of ethyl 4-(3-benzyloxycarbonyl-1-indolyl)-butyrate and 10% palladium carbon in ethanol was stirred at room temperature for 1.5 hours under a hydrogen atmosphere. Removal of the catalyst and evaporation of the solvent afforded the object product.

$^1$H-NMR (CDCl$_3$, 200 MHz) δ: 8.25 (1H, m), 7.92 (1H, s), 7.25–7.5 (3H, m), 4.28 (2H, t, J=7 Hz), 4.15 (2H, q, J=7 Hz), 2.1–2.4 (4H, m), 1.27 (3H, t, J=7 Hz)

EXAMPLE 1

A mixture of 3-heptanoylindole (1.0 g) obtained in Pre. Ex. 1, ethyl 4-bromobutyrate (0.86 g) and potassium carbonate (1.0 g) in dimethyl formamide (DMF) (25 ml) was stirred at room temperature for 16 hours. The mixture was poured into a mixture of hydrochloric acid (100 ml) and ethyl acetate (AcOEt) (50 ml). The organic layer was washed with water, dried over MgSO$_4$ and evaporated. The residue was chromatographed on a silica gel column with a mixture of n-hexane and AcOEt (3:1) as eluent to give ethyl 4-(3-heptanoyl-1-indolyl)butyrate as a colorless oil. (1.53 g)

$^1$H-NMR (CDCl$_3$) δ: 8.40 (1H, m), 7.75 (1H, s), 7.2–7.4 (3H, m), 4.25 (2H, t, J=7 Hz), 4.15 (2H, q, J=7 Hz), 2.85 (2H, t, J=7 Hz), 2.1–2.4 (4H, m), 1.7–1.9 (2H, m), 1.2–1.5 (9H, m), 0.90 (3H, m)

EXAMPLE 2

To a solution of ethyl 4-(3-heptanoyl-1-indolyl)butyrate (1.0 g) obtained in Ex. 1 in ethanol (30 ml) was added 1N-aqueous solution of sodium hydroxide (10 ml). The mixture was stirred at 40° C. for 2 hours and evaporated. To the residue was added a mixture of HCl (50 ml) and AcOEt (20 ml). The organic layer was washed with water, dried over MgSO$_4$ and evaporated. The residue was crystallized from IPE to give 4-(3-heptanoyl-1-indolyl) butyric acid as a white powder (0.58 g). mp: 58°–60° C.

$^1$H-NMR (CDCl$_3$) δ: 8.39 (1H, m), 7.76 (1H, s), 7.2–7.4 (3H, m), 4.25 (2H, t, J=7 Hz), 2.83 (2H, t, J=7 Hz), 2.40 (2H, t, J=7 Hz), 2.1–2.3 (2H, m), 1.7–1.9 (2H, m), 1.2–1.5 (6H, m), 0.88 (3H, m)

EXAMPLE 3

The procedure of Ex. 1 was repeated except that 3-octanoylindole obtained in Pre. Ex. 2 was used in place of 3-heptanoylindole to give ethyl 4-(3-octanoyl-1-indolyl)butyrate.

$^1$H-NMR (CDCl$_3$) δ: 8.40 (1H, m), 7.75 (1H, s), 7.2–7.4 (3H, m), 4.25 (2H, t, J=7 Hz), 4.15 (2H, q, J=7 Hz), 2.85 (2H, t, J=7 Hz), 2.1–2.4 (4H, m), 1.7–1.9 (2H, m), 1.2–1.5 (11H, m), 0.90 (3H, m)

EXAMPLE 4

The procedure of Ex. 2 was repeated except that ethyl 4-(3-octanoyl-1-indolyl)butyrate obtained in Ex. 3 was used in place of ethyl 4-(3-heptanoyl-1-indolyl)butyrate to give 4-(3-octanoyl-1-indolyl)butyric acid.

mp: 100°–102° C.

$^1$H-NMR (CDCl$_3$) δ: 8.39 (1H, m), 7.79 (1H, s), 7.2–7.4 (3H, m), 4.25 (2H, t, J=7 Hz), 2.83 (2H, t, J=7 Hz), 2.35 (2H, t, J=7 Hz), 2.1–2.3 (2H, m), 1.7–1.9 (2H, m), 1.2–1.5 (8H, m), 0.88 (3H, m)

EXAMPLE 5

The procedure of Ex. 1 was repeated except that 3-nonanoylindole obtained in Pre. Ex. 3 was used in place of 3-heptanoylindole to give ethyl 4-(3-nonanoyl-1-indolyl)butyrate.

$^1$H-NMR (CDCl$_3$) δ: 8.40 (1H, m), 7.75 (1H, s), 7.2–7.4 (3H, m), 4.25 (2H, t, J=7 Hz), 4.15 (2H, q, J=7 Hz), 2.85 (2H, t, J=7 Hz), 2.1–2.4 (4H, m), 1.7–1.9 (2H, m), 1.2–1.5 (13H, m), 0.90 (3H, m)

EXAMPLE 6

The procedure of Ex. 2 was repeated except that ethyl 4-(3-nonanoyl-1-indolyl)butyrate obtained in Ex. 5 was used in place of ethyl 4-(3-heptanoyl-1-indolyl)butyrate to give 4-(3-nonanyoyl-1-indolyl)butyric acid.

mp: 64°–65°

$^1$H-NMR (CDCl$_3$) δ: 8.39 (1H, m), 7.79 (1H, s), 7.2–7.4 (3H, m), 4.25 (2H, t, J=7 Hz), 2.83 (2H, t, J=7 Hz), 2.40 (2H, t, J=7 Hz), 2.1–2.3 (2H, m), 1.7–1.9 (2H, m), 1.2–1.5 (10H, m), 0.88 (3H, m)

EXAMPLE 7

The procedure of Ex. 1 was repeated except that 3-decanoylindole obtained in Pre. Ex. 4 was used in place of 3-heptanoylindole to give ethyl 4-(3-decanoyl-1-indolyl)butyrate.

$^1$H-NMR (CDCl$_3$) δ: 8.40 (1H, m), 7.75 (1H, s), 7.2–7.4 (3H, m), 4.25 (2H, t, J=7 Hz), 4.15 (2H, q, J=7 Hz), 2.85 (2H, t, J=7 Hz), 2.1–2.4 (4H, m), 1.7–1.9 (2H, m), 1.2–1.5 (15H, m), 0.85 (3H, m)

EXAMPLE 8

The procedure of Ex. 2 was repeated except that ethyl 4-(3-decanoyl-1-indolyl)butyrate obtained in Ex. 7 was used in place of ethyl 4-(3-heptanoyl-1-indolyl)butyrate to give 4-(3-decanoyl-1-indolyl)butyric acid.

mp: 89°–90° C.

$^1$H-NMR (CDCl$_3$) δ: 8.39 (1H, m), 7.76 (1H, s), 7.2–7.4 (3H, m), 4.25 (2H, t, J=7 Hz), 2.83 (2H, t, J=7 Hz), 2.40 (2H, t, J=7 Hz), 2.1–2.3 (2H, m), 1.7–1.9 (2H, m), 1.2–1.5 (12H, m), 0.85 (3H, m)

EXAMPLE 9

The procedure of Ex. 1 was repeated except that 3-undecanoylindole obtained in Pre. Ex. 5 was used in place of 3heptanoylindole to give ethyl 4-(3-undecanoyl-1-indolyl)butyrate.

$^1$H-NMR (CDCl$_3$) δ: 8.40 (1H, m), 7.75 (1H, s), 7.2–7.4 (3H, m), 4.25 (2H, t, J=7 Hz), 4.15 (2H, q, J=7 Hz), 2.85 (2H, t, J=7 Hz), 2.1–2.4 (4H, m), 1.7–1.9 (2H, m), 1.2–1.5 (17H, m), 0.90 (3H, m)

EXAMPLE 10

The procedure of Ex. 2 was repeated except that ethyl 4-(3-undecanoyl-1-indolyl)butyrate obtained in Ex. 9 was used in place of ethyl 4-(3-heptanoyl-1-indolyl)butyrate to give 4-(3-undecanoyl-1-indolyl))butyric acid.

mp: 71°–73° C.

$^1$H-NMR (CDCl$_3$) δ: 8.40 (1H, m), 7.80 (1H, s), 7.2–7.4 (3H, m), 4.25 (2H, t, J=7 Hz), 2.85 (2H, t, J=7 Hz), 2.40 (2H, t, J=7 Hz), 2.1–2.3 (2H, m), 1.7–1.9 (2H, m). 1.2–1.5 (14H, m), 0.89 (3H, m)

EXAMPLE 11

The procedure of Ex. 1 was repeated except that 3-dodecanoylindole obtained in Pre. Ex. 6 was used in place of 3-heptanoylindole to give ethyl 4-(3-dodecanoyl-1-indolyl)butyrate.

$^1$H-NMR (CDCl$_3$) δ: 8.40 (1H, m), 7.75 (1H, s), 7.2–7.4 (3H, m), 4.25 (2H, t, J=7 Hz), 4.15 (2H, q, J=7 Hz), 2.85 (2H, t, J=7 Hz), 2.1–2.4 (4H, m), 1.7–1.9 (2H, m), 1.2–1.5 (19H, m), 0.90 (3H, m)

EXAMPLE 12

The procedure of Ex. 2 was repeated except that ethyl 4-(3-dodecanoyl-1-indolyl)butyrate obtained in Ex. 11 was used in place of ethyl 4-(3-heptanoyl-1-indolyl)butyrate to give 4-(3-dodecanoyl-1-indolyl)butyric acid.

mp: 88°–90° C.

$^1$H-NMR (CDCl$_3$) δ: 8.40 (1H, m), 7.80 (1H, s), 7.2–7.4 (3H, m), 4.25 (2H, t, J=7 Hz), 2.85 (2H, t, J=7 Hz), 2.40 (2H, t, J=7 Hz), 2.1–2.3 (2H, m), 1.7–1.9 (2H, m), 1.2–1.5 (16H, m), 0.89 (3H, m)

EXAMPLE 13

The procedure of Ex. 1 was repeated except that 3-tridecanoylindole obtained in Pre. Ex. 7 was used in place of 3-heptanoylindole to give ethyl 4-(3-tridecanoyl-1-indolyl)butyrate.

$^1$H-NMR (CDCl$_3$) δ: 8.40 (1H, m), 7.75 (1H, s), 7.2–7.4 (3H, m), 4.25 (2H, t, J=7 Hz), 4.15 (2H, q, J=7 Hz), 2.85 (2H, t, J=7 Hz), 2.1–2.4 (4H, m), 1.7–1.9 (2H, m), 1.2–1.5 (21H, m), 0.90 (3H, m)

EXAMPLE 14

The procedure of Ex. 2 was repeated except that ethyl 4-(3-tridecanoyl-1-indolyl)butyrate obtained in Ex. 13 was used in place of ethyl 4-(3-heptanoyl-1-indolyl)butyrate to give 4-(3-tridecanoyl-1-indolyl)butyric acid.

mp: 76°–78° C.

$^1$H-NMR (CDCl$_3$) δ: 8.40 (1H, m), 7.80 (1H, s), 7.2–7.4 (3H, m), 4.25 (2H, t, J=7 Hz), 2.85 (2H, t, J=7 Hz), 2.40 (2H, t, J=7 Hz), 2.1–2.3 (2H, m), 1.7–1.9 (2H, m), 1.2–1.5 (18H, m), 0.89 (3H, m)

EXAMPLE 15

A mixture of 3-[8-(4-isobutylphenyl)undecanoyl]indole obtained in Pre. Ex. 8 (62 mg), ethyl 4-bromobutyrate (58 mg) and potassium carbonate (62 mg) in N,N-dimethylformamide (2 ml) was stirred at room temperature for 16 hours. After filtration, the solution was diluted with ethyl acetate, washed with water and brine, dried over magnesium sulfate and concentrated. The residue was chromatographed on a silica gel column (hexane-ethyl acetate, 4: 1) to give ethyl 4-[3-[8-(4-isobutylphenyl)-undecanoyl]-1-indolyl]butyrate as an oil. (48 mg)

$^1$H-NMR (CDCl$_3$, 300 MHz) δ: 8.40 (1H, m), 7.74 (1H, s), 7.25–7.45 (3H, m), 7.0–7.1 (4H, m), 4.25 (2H, t, J=7 Hz), 4.14 (2H, q, J=7 Hz), 2.81 (2H, t, J=7 Hz), 2.4–2.5 (3H, m), 2.33 (2H, t, J=7 Hz), 2.22 (2H, m), 1.05–1.9 (18H, m), 0.8–0.95 (12H, m)

EXAMPLE 16

A mixture of ethyl 4-[3-[8-(4-isobutylphenyl)undecanoyl] 1-indolyl]butyrate obtained in Ex. 15 (44 mg) and 1N solution of sodium hydroxide (0.5 ml) in ethanol (1 ml) and 1,4-dioxane (2 ml) was stirred at room temperature for 3 hours. The mixture was then acidified with diluted hydrochloric acid and extracted with ethyl acetate. The organic solution was washed with water and brine, and dried over magnesium sulfate. Evaporation of the solvent afforded 4-[3-[8-(4-isobutylphenyl)-undecanoyl]1-indolyl]butyric acid as an oil (41 mg).

$^1$H-NMR (CDCl$_3$, 300 MHz) δ: 8.39 (1H, m), 7.77 (1H, s), 7.25–7.45 (3H, m), 7.0–7.1 (4H, m), 4.27 (2H, t, J=7 Hz), 2.81 (2H, t, J=7 Hz), 2.35–2.5 (5H, m), 2.23 (2H, m), 1.05–1.9 (15H, m), 0.75–0.95 (9H, m)

EXAMPLE 17

The procedure of Ex. 15 was repeated except that 3-[6-(4isobutylphenyl)decanoyl]indole obtained in Pre. Ex. 9 was used in place of 3-[8-(4-isobutylphenyl)undecanoyl]indole to give ethyl 4-[3-[6-(4-isobutylphenyl)decanoyl]-1-indolyl] butyrate.

$^1$H-NMR (CDCl$_3$, 200 MHz) δ: 8.38 (1H, m), 7.70 (1H, s), 7.25–7.4 (3H, m), 7.03 (4H, s), 4.23 (2H, t, J=7 Hz), 4.13 (2H, q, J=7 Hz), 2.1–2.55 (7H, m), 1.45–1.95 (7H, m), 1.0–1.4 (9H, m), 0.75–0.95 (9H, m)

EXAMPLE 18

The procedure of Ex. 16 was repeated except that ethyl 4-[3-[6-(4-isobutylphenyl)decanoyl]-1-indolyl]butyrate obtained in Ex. 17 was used in place of ethyl 4-[3-[8-(4-isobutylphenyl)undecanoyl]-1-indolyl]butyrate to give 4-[3-6-(4-isobutylphenyl)decanoyl]-1-indolyl]butyric acid.

$^1$H-NMR (CDCl$_3$, 200 MHz) δ: 8.38 (1H, m), 7.72 (1H, s), 7.25–7.45 (3H, m), 7.03 (4H, s), 4.26 (2H, t, J=7 Hz), 2.78 (2H, t, J=7.5 Hz), 2.35–2.55 (5H, m), 2.21 (2H, m), 1.0–1.95 (13H, m), 0.75–0.95 (9H, m)

EXAMPLE 19

The procedure of Ex. 15 was repeated except that 3-[7-(4isobutylphenyl)undecanoyl]indole obtained in Pre. Ex. 10 was used in place of 3-[8-(4-isobutylphenyl)undecanoyl] indole to give ethyl 4-[3-[7-(4-isobutylphenyl)undecanoyl] -1-indolyl]butyrate.

¹H-NMR (CDCl₃, 200 MHz) δ: 8.38 (1H, m), 7.72 (1H, s), 7.25–7.45 (3H, m), 6.95–7.1 (4H, m), 4.24 (2H, t, J=7 Hz), 4.14 (2H, q, J=7 Hz), 2.78 (2H, t, J=7.5 Hz), 2.1–2.5 (7H, m), 1.0–2.0 (18H, m), 0.75–0.95 (9H, m)

EXAMPLE 20

The procedure of Ex. 16 was repeated except that ethyl 4-[3-[7-(4-isobutylphenyl)undecanoyl]-1-indolyl]butyrate obtained in Ex. 19 was used in place of ethyl 4-[3-[8-(4-isobutylphenyl)undecanoyl]-1-indolyl]butyrate to give 4-[3-[7-(4isobutylphenyl)undecanoyl]-1-indolyl]butyric acid.

¹H-NMR (CDCl₃, 200 MHz) δ: 8.38 (1H, m), 7.73 (1H, s), 7.2–7.45 (3H, m), 6.95–7.1 (4H, m), 4.24 (2H, t, J=7 Hz), 2.79 (2H, t, J=7.5 Hz), 2.3–2.5 (5H, m), 2.21 (2H, m), 1.0–2.0 (15H, m), 0.75–0.95 (3H, m)

EXAMPLE 21

The procedure of Ex. 15 was repeated except that 3-(6-butyldecanoyl)indole obtained in Pre. Ex. 11 was used in place of 3-[8-(4-isobutylphenyl)undecanoyl]indole to give ethyl 4-[3(6-butyldecanoyl)-1-indolyl]butyrate.

¹H-NMR (CDCl₃, 200 MHz) δ: 8.40 (1H, m), 7.77 (1H, s), 7.2–7.45 (3H, m), 4.27 (2H, t, J=7 Hz), 4.15 (2H, q, J=7 Hz), 2.84 (2H, t, J=7.5 Hz), 2.1–2.4 (4H, m), 1.75 (2H, m), 1.1–1.5 (20H, m), 0.88 (6H, t, J=6.5 Hz)

EXAMPLE 22

The procedure of Ex. 16 was repeated except that ethyl 4-[3-(6-butyldecanoyl)-1-indolyl]butyrate obtained in Ex. 21 was used in place of ethyl 4-[3-[8-(4-isobutylphenyl)undecanoyl]1-indolyl]butyrate to give 4-[3-(6-butyldecanoyl)-1-indolyl]butyric acid.

¹H-NMR (CDCl₃, 200 MHz) δ: 8.40 (1H, m), 7.78 (1H, s), 7.2–7.45 (3H, m), 4.28 (2H, t, J=7 Hz), 2.86 (2H, t, J=7.5 Hz), 2.42 (2H, t, J=7 Hz), 2.23 (2H, m), 1.75 (2H, m), 1.1–1.5 (17H, m), 0.88 (6H, t, J=6.5 Hz)

EXAMPLE 23

The procedure of Ex. 15 was repeated except that 3-[5-(4-isobutylphenyl)valeryl]indole obtained in Pre. Ex. 12 was used in place of 3-[8-(4-isobutylphenyl)undecanoyl]indole to give ethyl 4-[3-[5-(4-isobutylphenyl)valeryl]-1-indolyl]butyrate.

¹H-NMR (CDCl₃, 200 MHz) δ: 8.39 (1H, m), 7.72 (1H, s), 7.25–7.45 (3H, m), 7.0–7.15 (4H, m), 4.24 (2H, t, J=7 Hz), 4.15 (2H, q, J=7 Hz), 2.88 (2H, t, J=7 Hz), 2.65 (2H, t, J=7 Hz), 2.42 (2H, d, J=7 Hz), 2.1–2.4 (4H, m), 1.6–1.95 (5H, m), 1.27 (3H, t, J=7 Hz), 0.89 (6H, d, J=7 Hz)

EXAMPLE 24

The procedure of Ex. 16 was repeated except that ethyl 4-[3-[5-(4-isobutylphenyl)valeryl]-1-indolyl]butyrate obtained in Ex. 23 was used in place of ethyl 4-[3-[8-(4-isobutylphenyl)undecanoyl]-1-indolyl]butyrate to give 4-[3-[5-(4-isobutylphenyl)valeryl]-1-indolyl]butyric acid.

¹H-NMR (CDCl₃, 200 MHz) δ: 8.39 (1H, m), 7.75 (1H, s), 7.25–7.45 (3H, m), 7.0–7.15 (4H, m), 4.27 (2H, t, J=7 Hz), 2.88 (2H, t, J=7 Hz), 2.65 (2H, t, J=7 Hz), 2.35–2.5 (4H, m), 2.21 (2H, m), 1.65–1.95 (5H, m), 0.89 (6H, t, J=7 Hz)

EXAMPLE 25

The procedure of Ex. 15 was repeated except that 3-(4-methylvaleryl)indole obtained in Pre. Ex. 13 was used in place of 3-[8-(4-isobutylphenyl)undecanoyl]indole to give ethyl 4-[3-(4-methylvaleryl)-1-indolyl]butyrate.

¹H-NMR (CDCl₃, 200 MHz) δ: 8.40 (1H, m), 7.77 (1H, s), 7.25–7.45 (3H, m), 4.27 (2H, t, J=7 Hz), 4.14 (2H, q, J=7 Hz), 2.86 (2H, t, J=7.5 Hz), 2.1–2.4 (4H, m), 1.55–1.8 (3H, m), 1.27 (3H, t, J=7 Hz), 0.97 (6H, d, J=6.5 Hz)

EXAMPLE 26

The procedure of Ex. 16 was repeated except that ethyl 4-[3-(4-methylvaleryl)-1-indolyl]butyrate obtained in Ex. 25 was used in place of ethyl 4-[3-[8-(4-isobutylphenyl)undecanoyl]1-indolyl]butyrate to give 4-[3-(4-methylvaleryl)-1-indolyl]butyric acid.

¹H-NMR (CDCl₃, 200 MHz) δ: 8.39 (1H, m), 7.78 (1H, s), 7.2–7.45 (3H, m), 4.28 (2H, t, J=7 Hz), 2.86 (2H, t, J=7.5 Hz), 2.42 (2H, t, J=7 Hz), 2.23 (2H, m), 1.55–1.8 (3H, m), 0.96 (6H, d, J=6.5 Hz)

EXAMPLE 27

The procedure of Ex. 15 was repeated except that 3-linoleylindole obtained in Pre. Ex. 14 was used in place of 3-[8-(4-isobutylphenyl)undecanoyl]indole to give ethyl 4-(3-linoleyl-1-indolyl)butyrate.

¹H-NMR (CDCl₃, 200 MHz) δ: 8.40 (1H, m), 7.76 (1H, s), 7.2–7.45 (3H, m), 5.25–5.45 (4H, m), 4.27 (2H, t, J=7 Hz), 4.15 (2H, q, J=7 Hz), 2.7–2.9 (4H, m), 1.95–2.4 (8H, m), 1.78 (2H, m), 1.2–1.5 (17H, m), 0.89 (3H, t, J=7 Hz)

EXAMPLE 28

The procedure of Ex. 16 was repeated except that ethyl 4-(3-linoleyl-1-indolyl)butyrate obtained in Ex. 27 was used in place of ethyl 4-[3-[8-(4-isobutylphenyl)undecanoyl]-1-indolyl]butyrate to give 4-(3-linoleyl-1-indolyl)butyric acid.

¹H-NMR (CDCl₃, 200 MHz) δ: 8.38 (1H, m), 7.78 (1H, s), 7.2–7.45 (3H, m), 5.25–5.45 (4H, m), 4.28 (2H, t, J=7 Hz), 2.7–2.9 (4H, m), 2.42 (2H, t, J=7 Hz), 2.22 (2H, m), 1.9–2.15 (4H, m), 1.77 (2H, m), 1.15–1.5 (14H, m), 0.89 (2H, t, J=7 Hz)

EXAMPLE 29

The procedure of Ex. 1 was repeated except that 3-(3,7-dimethyl-6-octenoyl)indole obtained in Pre. Ex. 15 was used in place of 3-heptanoylindole to give ethyl 4-[3-(3,7-dimethyl-6-octenoyl)-1-indolyl]butyrate as an oil.

¹H-NMR (CDCl₃, 200 MHz) δ: 8.41 (1H, m), 7.72 (1H, s), 7.15–7.45 (3H, m), 5.10 (1H, t, J=7 Hz), 4.0–4.3 (4H, m), 2.5–2.9 (2H, m), 1.85–2.4 (7H, m), 1.1–1.75 (11H, m), 0.98 (3H, d, J=7 Hz)

EXAMPLE 30

The procedure of Ex. 16 was repeated except that ethyl 4-[3-(3,7-dimethyl-6-octenoyl)-1-indolyl]butyrate obtained in Ex. 29 was used in place of ethyl 4-[3-[8-(4-isobutylphenyl)undecanoyl]-1-indolyl]butyrate to give 4-[3-(3,7-dimethyl-6-octenoyl)-1-indolyl]butyric acid as an oil.

¹H-NMR (CDCl₃, 200 MHz) δ: 8.42 (1H, in), 7.76 (1H, s), 7.2–7.45 (3H, m), 5.10 (1H, t, J=7 Hz), 4.28 (2H, t, J=7 Hz), 2.55–2.9 (2H, m), 2.42 (2H, t, J=7 Hz), 1.85–2.35 (5H, m), 1.15–1.75 (8H, m), 0.98 (3H, d, J=7 Hz)

EXAMPLE 31

A mixture of 4-[3-(3,7-dimethyl-6-octenoyl)-1-indolyl] butyric acid (267 mg) obtained in Ex. 30 and 10% palladium carbon (80 mg) in methanol was stirred at room temperature for 3 hours under a hydrogen atmosphere at 3 atm. The catalyst was removed and the solvent was evaporated. The residue was chromatographed on a silica gel column (3–10% methanol in chloroform as an eluent) to give 4-[3-(3,7-dimethyloctanoyl)-1-indolyl]butyric acid (142 mg) as an oil.

$^1$H-NMR (CDCl$_3$, 200 MHz) δ: 8.42 (1H, m), 7.76 (1H, s), 7.2–7.45 (3H, m), 4.28 (2H, t, J=7 Hz), 2.55–2.9 (2H, m), 2.42 (2H, t, J=7 Hz), 2.1–2.35 (3H, m), 1.05–1.65 (7H, m), 0.98 (3H, d, J=7 Hz), 0.86 (6H, d, J=7 Hz)

EXAMPLE 32

The procedure of Ex. 1 was repeated except that trans-3-(4-pentylcyclohexylcarbonyl)indole obtained in Pre. Ex. 16 was used in place of 3-heptanoylindole to give trans-ethyl 4-[3-(4-pentylcylohexylcarbonyl)-1-indolyl]butyrate.

$^1$H-NMR (CDCl$_3$, 200 MHz) δ: 8.40 (1H, m), 7.78 (1H, s), 7.2–7.45 (3H, m), 4.26 (2H, t, J=7 Hz), 4.15 (2H, q, J=7 Hz), 2.98 (1H, m), 2.15–2.4 (4H, m), 1.5–2.0 (6H, m), 0.85–1.45 (17H, m)

EXAMPLE 33

The procedure of Ex. 16 was repeated except that trans-ethyl 4-[3-(4-pentylcyclohexylcarbonyl)-1-indolyl]butyrate obtained in Ex. 32 was used in place of ethyl 4-[3-[8-(4-isobutylphenyl) undecanoyl]-1-indolyl]butyrate to give trans-4-[3-(4-pentylcyclohexylcarbonyl)-1-indolyl]butyric acid.

$^1$H-NMR (CDCl$_3$, 200 MHz) δ: 8.40 (1H, m), 7.79 (1H, s), 7.2–7.45 (3H, m), 4.28 (2H, t, J=7 Hz), 2.99 (1H, m), 2.42 (2H, t, J=7 Hz), 2.24 (2H, m), 1.8–2.0 (4H, 1.5–1.75 (2H, m), 0.8–1.45 (14H, m)

EXAMPLE 34

The procedure of Ex. 1 was repeated except that 3-[3-[1-(4-isobutylphenyl) pentyloxy]propionyl]indole obtained in Pre. Ex. 17 was used in place of 3-heptanolindole to give ethyl 4-[3-[3-[1-( 4-isobutyl-phenyl)pentyloxy]propionyl]-1-indolyl]butyrate as an oil.

$^1$H-NMR (CDCl$_3$, 200 MHz) δ: 8.37 (1H, m), 7.77 (1H, s), 7.2–7.45 (3H, m), 7.18 (2H, d, J=8.5 Hz), 7.08 (2H, d, J=8.5 Hz), 4.05–4.3 (4H, m), 3.75 (2H, t, J=7 Hz), 2.95–3.3 (2H, m), 2.45 (2H, d, J=7 Hz), 2.1–2.4 (4H, m), 1.45–2.0 (3H, m), 1.05–1.4 (7H, m), 0.75–0.95 (9H, m)

EXAMPLE 35

The procedure of Ex. 16 was repeated except that ethyl 4-[3-[3-[1-(4-isobutylphenyl)pentyloxy]propionyl]-1-indolyl]butyrate obtained in Ex. 34 was used in place of ethyl 4-[3-[8(4-isobutylphenyl)undecanoyl]-1-indolyl]butyrate to give 4-[3-[3-[1-(4-isobutylphenyl)pentyloxy]propionyl]-1-indolyl]butyric acid as an oil.

$^1$H-NMR (CDCl$_3$, 200 MHz) δ: 8.38 ( 1H, m), 7.78 (1n, s), 7.2–7.45 (3H, m), 7.18 (2H, d, J =8.5 Hz), 7.08 ( 2H, d, J =8.5 Hz), 4.15–4.3 (3H, m), 3.75 (2H, t, J=7 Hz), 2.95–3.3 (2H, m), 2.3–2.5 (4H, m), 2.21 (2H, m), 1.5–1.95 (3H, m), 1.05–1.4 (4H, m), 0.75–0.95 (9H, m)

EXAMPLE 36

The procedure of Ex. 34 was repeated except that 3-[5-[1-(4-isobutylphenyl)pentyloxy]valerylindole obtained in Pre. Ex. 18 was used in place of 3-[3-[1-(4-isobutylphenyl-)pentyloxy]-propionyl]-1-indole to give ethyl 4-[3-[5-[1-(4-isobutylphenyl)pentyloxy]valeryl]-1-indolyl]butyrate.

$^1$H-NMR (CDCl$_3$, 200 MHz) δ: 8.38 (1H, m), 7.73 (1H, s), 7.2–7.45 (3H, m), 7.18 (2H, d, J=8.5 Hz), 7.08 (2H, d, J=8.5 Hz), 4.05–4.3 (5H, m), 3.15–3.45 (2H, m), 2.85 (2H, t, J=7 Hz), 2.45 (2H, d, J=7 Hz), 2.1–2.4 (4H, m), 1.1–2.0 (14H, m), 0.75–0.95 (9H, m)

EXAMPLE 37

The procedure of Ex. 16 was repeated except that ethyl 4-[3-[5-[1-(4-isobutylphenyl)pentyloxy]valeryl]-1-indolyl] butyrate obtained in Ex. 36 was used in place of ethyl 4-[3-[8-(4isobutylphenyl) undecanoyl]-1-indolyl]butyrate to give 4-[3-[5-[1-(4-isobutylphenyl)pentyloxy]valeryl]-1-indolyl]butyric acid.

$^1$H-NMR (CDCl$_3$, 200 MHz) δ: 8.38 (1 H, m), 7.73 (1 H, s), 7.2–7.45 (3H, m), 7.18 (2H, d, J=8.5 MHz), 7.08 (2H, d, J=8.5 Hz), 4.28 (2H, t, J=7 Hz), 4.14 (1H, t, J=7 Hz), 3.15–3.45 (2H, m), 2.83 (2H, t, J=7 Hz), 2.1–2.5 (6H, m), 1.05–2.0 (11H, m), 0.75–0.95 (9H, m)

EXAMPLE 38

The procedure of Ex. 1 was repeated except that (E)-3-[4-[1-(4-isobutylphenyl)pentyloxy]-2-butenoyl]indole obtained in Step 4 of Pre. Ex. 19 was used in place of 3-heptanoylindole, and 4-methoxybenzyl 4-bromobutyrate obtained in Step 5 of Pre. Ex. 19 was used in place of 4-bromobutyrate to give 4-methoxybenzyl (E)-4-[3-[4-[1-(4-isobutylphenyl)pentyloxy]-2-butenoyl]1-indolyl]butyrate as an oil.

$^1$H-NMR (CDCl$_3$, 200 MHz) δ: 8.48 (1H, m), 7.77 (1H, s), 6.85–7.35 (11H, m), 5.07 (2H, s), 3.95–4.35 (5H, m), 3.80 (3H, s), 2.1–2.5 (6H, m), 1.15–2.0 (7H, m), 0.8–0.95 (9H, m)

EXAMPLE 39

A mixture of 4-methoxybenzyl (E)-4-[3-[4-[1-(4-isobutylphenyl)pentyloxy]-2-butenoyl]-1-indolyl]butyrate (86 mg) obtained in Ex. 38, ammonium formate (90 mg) and 10% palladium carbon (90 mg) in methanol and N,N-dimethylformamide was stirred at room temperature for 1 hour. The catalyst was removed and the solvent was evaporated. The residue was diluted with ethyl acetate, washed with water and brine, dried over magnesium sulfate and concentrated. The residue was chromatographed on a silica gel column to give 4-[3-[4-[1-(4-isobutylphenyl)pentyloxy] -1-indolyl]butyric acid as an oil.

$^1$H-NMR (CDCl$_3$, 200 MHz) δ: 8.38 (1H, m), 7.80 (1H, s), 7.2–7.45 (3H, m), 7.18 (2H, d, J=8.5 Hz), 7.08 (2H, d, J=8.5 Hz), 4.1–4.35 (3H, m), 3.39 (2H, m), 2.95 (2H, m), 1.1–2.5 (15H, m), 0.75–0.95 (9H, m)

EXAMPLE 40

The procedure of Ex. 1 was repeated except that 3-(3-ethoxycarbonylpropionyl)indole obtained in Pre. Ex. 20 was used in place of 3-heptanoylindole to give ethyl 4-[3-(3-ethoxycarbonylpropionyl)-1-indolyl]butyrate as a solid.

¹H-NMR (CDCl₃, 200 MHz) δ: 8.38 (1H, m), 7.83 (1H, s), 7.2–7.45 (3H, m), 4.1–4.3 (6H, m), 3.22 (2H, t, J=7 Hz), 2.80 (2H, t, J=7 Hz), 2.1–2.4 (4H, m), 1.27 (6H, m)

EXAMPLE 41

The procedure of Ex. 16 was repeated except that ethyl 4-[3-(3-ethoxycarbonylpropionyl)-1-indolyl]butyrate obtained in Ex. 40 was used in place of 4-[3-[8-(4-isobutylphenyl)undecanoyl]-1-indolyl]butyrate to give 4-[3-(3-carboxy-propionyl)-1-indolyl]butyric acid as a powder.

¹H-NMR (DMSO-d₆, 200 MHz) δ: 8.41 (1H, s), 8.19 (1H, d, J=8 Hz), 7.60 (1H, d, J=8 Hz), 7.1–7.4 (2H, m), 4.28 (2H, t, J=7 Hz), 3.10 (2H, t, J=7 Hz), 2.58 (2H, t, J=7 Hz), 2.27 (2H, t, J=7 Hz), 2.03 (2H, m)

EXAMPLE 42

The procedure of Ex. 1 was repeated except that 3-(11-benzyloxycarbonylundecanoyl)indole obtained in Pre. Ex. 21 was used in place of 3-heptanoylindole to give ethyl 4-[3-(11-benzyloxycarbonylundecanoyl)-1-indolyl]butyrate as an oil.

¹H-NMR (CDCl₃, 200 MHz) δ: 8.40 (1H, m), 7.77 (1H, s), 7.2–7.45 (8H, m), 5.12 (2H, s), 4.26 (2H, t, J=7 Hz), 4.15 (2H, q, J=7 Hz), 2.85 (2H, t, J=7 Hz), 2.1–2.4 (6H, m), 1.55–1.85 (4H, m), 1.15–1.5 (12H, m)

EXAMPLE 43

The procedure of Ex. 16 was repeated except that ethyl 4-[3-(11-benzyloxycarbonylundecanoyl)-1-indolyl]butyrate was used in place of ethyl 4-[3-[8-(4-isobutylphenyl)undecanoyl]-lindolyl]butyrate to give 4-[3-(11-carboxyundecanoyl)-1-indolyl]butyric acid as a powder.

¹H-NMR (DMSO-d₆, 200 MHz) δ: 8.39 (1H, s), 8.21 (1H, d, J=7 Hz), 7.60 (1H, d, J=7 Hz), 7.15–7.35 (2H, m), 4.28 (2H, t, J=7 Hz), 2.82 (2H, t, J=7 Hz), 1.95–2.3 (6H, m), 1.1–1.75 (16H, m)

EXAMPLE 44

The procedure of Ex. 1 was repeated except that (E)-3-(2-nonenoyl) indole obtained in Pre. Ex. 22 was used in place of 3-heptanoylindole, and 4-methoxybenzyl 4-bromobutyrate obtained in Step 5 of Pre. Ex. 19 was used in place of 4-bromobutyrate to give (E)-4-methoxybenzyl 4-[3-(2-nonenoyl)-1-indolyl]butyrate as an oil.

¹H-NMR (CDCl₃, 200 MHz) δ: 8.47 (1H, m), 7.76 (1H, s), 7.2–7.4 (5H, m), 7.06 (1H, dt, J=7 Hz, 16 Hz), 6.89 (2H, d, J=8.5 Hz), 6.73 (1H, d, J=16 Hz), 5.06 (2H, s), 4.23 (2H, t, J=7 Hz), 3.81 (3H, s), 2.1–2.45 (6H, m), 1.2–1.6 (8H, m), 0.90 (3H, t, J=7 Hz)

EXAMPLE 45

To a solution of (E)-4-methoxybenzyl 4-[3-(2-nonenoyl)-1-indolyl]butyrate (312 mg) obtained in Ex. 44 and anisole (0.3 ml) in dichloromethane was added trifluoroacetic acid (1 ml). After being stirred at room temperature for 1 hour, the solvent was evaporated. The residue was diluted with ethyl acetate, washed with water and brine, dried over magnesium sulfate and concentrated. The residue was chromatographed on a silica gel column (4% methanol in chloroform as an eluent) to give (E)-4-[3-(2-nonenoyl)-1-indolyl]butyric acid as an oil.

¹H-NMR (CDCl₃, 200 MHz) δ: 8.47 (1H, m), 7.81 (1H, s), 7.2–7.45 (3H, m), 7.06 (1H, dt, J=7 Hz, 16 Hz), 6.76 (1H, d, J=16 Hz), 4.28 (2H, t, J=7 Hz), 2.1–2.5 (6H, m), 1.15–1.65 (8H, m), 0.90 (3H, t, J=7 Hz)

EXAMPLE 46

The procedure of Ex. 1 was repeated except that (E)-3-(2-decenoyl)indole obtained in Pre. Ex. 23 was used in place of 3-heptanoylindole, and 4-methoxybenzyl 4-bromobutyrate was used in place of 4-bromobutyrate to give (E)-4-methoxybenzyl 4-[3-(2-decenoyl)-1-indolyl]butyrate.

¹H-NMR (CDCl₃, 200 MHz) δ: 8.47 (1H, m), 7.76 (1H, s), 7.2–7.4 (3H, m), 7.05 (1H, dt, J=7 Hz, 16 Hz), 6.89 (2H, d, J=8.5 Hz), 6.73 (1H, d, J=16 Hz), 5.07 (2H, s), 4.23 (2H, t, J=7 Hz), 3.81 (3H, s), 2.1–2.45 (6H, m), 1.2–1.6 (10H, m), 0.89 (3H, t, J=7 Hz)

EXAMPLE 47

The procedure of Ex. 45 was repeated except that (E)-4-methoxybenzyl 4-[3-(2-decenoyl)-1-indolyl]butyrate obtained in Ex. 46 was used in place of (E)-4-methoxybenzyl 4-[3-(2-none-noyl)-1-indolyl]butyrate to give (E)-4-[3-(2-decenoyl)-1-indolyl]butyric acid.

¹H-NMR (CDCl₃, 200 MHz) δ: 8.48 (1H, m), 7.81 (1H, s), 7.2–7.45 (3H, m), 7.07 (1H, dt, J=7 Hz, 16 Hz), 6.76 (1H, d, J=16 Hz), 4.28 (2H, t, J=7 Hz), 2.15–2.5 (6H, m), 1.1–1.65 (10H, m), 0.89 (3H, t, J=7 Hz)

EXAMPLE 48

The procedure of Ex. 1 was repeated except that (E)-3-(2-undecenoyl)indole obtained in Pre. Ex. 24 was used in place of 3-heptanoylindole, and 4-methoxybenzyl 4-bromobutyrate was used in place of 4-bromobutyrate to give (E)-4-methoxybenzyl 4-[3-(2-undecenoyl)-1-indolyl]butyrate.

¹H-NMR (CDCl₃, 200 MHz) δ: 8.47 (1H, m), 7.76 (1H, s), 7.2–7.4 (5H, m), 7.05 (1H, dt, J=7 Hz, 16 Hz), 6.89 (2H, d, J=8.5 Hz), 6.73 (1H, d, J=16 Hz), 5.07 (2H, s), 4.23 (2H, t, J=7 Hz), 3.81 (3H, s), 2.1–2.45 (6H, m), 1.15–1.6 (12H, m), 0.89 (3H, t, J=7 Hz)

EXAMPLE 49

The procedure of Ex. 45 was repeated except that (E)-4-methoxybenzyl 4-[3-(2-undecenoyl)-1-indolyl]butyrate obtained in Ex. 48 was used in place of (E)-4-methoxybenzyl 4-[3-(2-none-noyl)-1-indolyl]butyrate to give (E)-4-[3-(2-undecenoyl)-1-indolyl]butyric acid.

¹H-NMR (CDCl₃, 200 MHz) δ: 8.47 (1H, m), 7.81 (1H, s), 7.2–7.45 (3H, m), 7.06 (1H, dt, J=7 Hz, 16 Hz), 6.76 (1H, d, J=16 Hz), 4.38 (2H, t, J=7 Hz), 2.1–2.5 (6H, m), 1.1–1.6 (12H, m), 0.88 (3H, t, J=7 Hz)

EXAMPLE 50

The procedure of Ex. 1 was repeated except that (E)-3-(2-methyl-2-undecenyl)indole obtained in Pre. Ex. 25 was used in place of 3-heptanoylindole, and 4-methoxybenzyl 4-bromobutyrate was used in place of 4-bromobutyrate to give (E)-4-methoxybenzyl 4-[3-(2-methyl-2-undecenoyl)-1-indolyl]butyrate as an oil.

¹H-NMR (CDCl₃, 200 MHz) δ: 7.32 (1H, m), 7.52 (1H, s), 7.2–7.4 (3H, m), 6.89 (2H, d, J=8.5 Hz), 6.28 (1H, dt, J=1 Hz, 7 Hz), 5.05 (2H, s), 4.21 (2H, t, J=7 Hz), 3.81 (3H, s), 2.1–2.4 (6H, m), 1.99 (3H, d, J=7 Hz), 1.15–1.6 (12H, m), 0.89 (3H, t, J=7 Hz)

EXAMPLE 51

A solution of (E)-4-methoxybenzyl 4-[3-(2-methyl-2-undecenoyl)-1-indolyl]butyrate obtained in Ex. 50 in formic acid was stirred at room temperature for 3 hours. The mixture was concentrated, diluted with ethyl acetate, washed with water and brine, dried over magnesium sulfate and concentrated. The residue was chromatographed on a silica gel column to give (E)-4-[3-(2-methyl-2-undecenoyl)-1-indolyl]butyric acid as an oil.

$^1$H-NMR (CDCl$_3$, 200 MHz) δ: 8.30 (1H, m), 7.55 (1H, s), 7.2–7.45 (3H, m), 6.30 (1H, dt, J=1 Hz, 7 Hz), 4.37 (2H, t, J=7 Hz), 2.1–2.5 (6H, m), 1.99 (3H, d, J=1 Hz), 1.15–1.55 (12H, m), 0.88 (3H, t, J=7 Hz)

EXAMPLE 52

A mixture of (E)-4-methoxybenzyl 4-[3-(2-methyl-2-undecenoyl)-1-indolyl]butyrate (201 mg) obtained in Ex. 50, ammonium formate (0.25 g) and 10% palladium carbon (0.1 g) in methanol and N,N-dimethylformamide was stirred at room temperature for 3 hours. The catalyst was removed and the solvent was evaporated. The residue was diluted with ethyl acetate, washed with water and brine, dried over magnesium sulfate and concentrated. The residue was chromatographed on a silica gel column to give (E)-4-[3-(2-methylundecanoyl)-lindolyl]butyric acid as an oil.

$^1$H-NMR (CDCl$_3$, 200 MHz) δ: 8.45 (1H, m), 7.80 (1H, s), 7.25–7.45 (3H, m), 4.28 (2H, t, J=7 Hz), 3.20 (1H, m), 2.42 (2H, t, J=7 Hz), 2.23 (2H, m), 1.83 (1H, m), 1.1–1.6 (18H, m), 0.87 (3H, t, J=7 Hz)

EXAMPLE 53

The procedure of Ex. 1 was repeated except that 3-(3-heptyl-2-decenoyl)indole obtained in Pre. Ex. 26 was used in place of 3-heptanoylindole, and 4-methoxybenzyl 4-bromobutyrate was used in place of 4-bromobutyrate to give 4-methoxybenzyl 4-[3-(3-heptyl-2-decenoyl)-1-indolyl]butyrate as an oil.

$^1$H-NMR (CDCl$_3$, 200 MHz) δ: 8.45 (1H, m), 7.70 (1H, s), 7.2–7.35 (3H, m), 6.89 (2H, d, J=8.5 Hz), 6.52 (1H, s), 5.06 (2H, s), 4.22 (2H, t, J=7 Hz), 3.81 (3H, s), 2.68 (2H, t, J=7 Hz), 2.1–2.45 (6H, m), 1.15–1.65 (20H, m), 0.8–1.0 (6H, m)

EXAMPLE 54

The procedure of Ex. 45 was repeated except that 4-methoxybenzyl 4-[3-(3-heptyl-2-decenoyl)-1-indolyl]butyrate obtained in Ex. 53 was used in place of (E)-4-methoxybenzyl 4-[3-(2-nonenoyl)-1-indolyl]butyrate to give 4-[3-(3-heptyl-2-decenoyl)-1-indolyl]butyric acid as an oil.

$^1$H-NMR (CDCl$_3$, 200 MHz) δ: 8.45 (1H, m), 7.75 (1H, s), 7.2–7.45 (3H, m), 6.55 (1H, s), 4.26 (2H, t, J=7 Hz), 2.1–2.75 (8H, m), 1.1–1.7 (20H, m), 0.75–1.0 (6H, m)

EXAMPLE 55

The procedure of Ex. 52 was repeated except that 4-methoxybenzyl 4-[3-(3-heptyl-2-decenoyl)-1-indolyl]butyrate obtained in Ex. 53 was used in place of (E)-4-methoxybenzyl 4-[3-(2-methyl-2-nonenoyl)-1-indolyl]butyrate to give 4-[3-(3-heptyldecanoyl)-1-indolyl]butyric acid as an oil.

$^1$H-NMR (CDCl$_3$, 200 MHz) δ: 8.42 (1H, m), 7.76 (1H, s), 7.2–7.45 (3H, m), 4.27 (2H, t, J=7 Hz), 2.76 (2H, d, J=7 Hz), 2.42 (2H, t, J=7 Hz), 2.05–2.35 (3H, m), 1.15–1.45 (24H, m), 0.87 (6H, t, J=7 Hz)

EXAMPLE 56

The procedure of Ex. 1 was repeated except that (E)-3-(4isobutylcinnamoyl)indole obtained in Pre. Ex. 27 was used in place of 3-heptanoylindole to give (E)-ethyl 4-[3-(4-isobutyl-cinnamoyl)- 1-indolyl]butyrate as an oil.

$^1$H-NMR (CDCl$_3$, 200 MHz) δ: 8.53 (1H, m), 7.91 (1H, s), 7.82 (1H, d, J=16 Hz), 7.58 (2H, d, J=8.5 Hz), 7.25–7.45 (4H, m), 7.20 (2H, d, J=8.5 Hz), 4.30 (2H, t, J=7 Hz), 4.15 (2H, q, J=7 Hz), 2.52 (2H, d, J=7 Hz), 2.15–2.4 (4H, m), 1.90 (1H, m), 1.27 (3H, t, J=7 Hz), 0.93 (6H, d, J=7 Hz)

EXAMPLE 57

The procedure of Ex. 16 was repeated except that (E)-ethyl 4-[3-(4-isobutylcinnamoyl)-1-indolyl]butyrate obtained in Ex. 56 was used in place of ethyl 4-[3-[8-(4-isobutylphenyl)undecanoyl]-1-indolyl]butyrate to give (E)-4-[3-(4-isobutylcinnamoyl)-1-indolyl]butyric acid as a powder.

$^1$H-NMR (CDCl$_3$, 200 MHz) δ: 8.52 (1H, m), 7.93 (1H, s), 7.82 (1H, d, J=16 Hz), 7.57 (2H, d, J=8.5 Hz), 7.25–7.45 (4H, m), 7.18 (2H, d, J=8.5 Hz), 4.30 (2H, t, J=7 Hz), 2.35 (4H, m), 2.25 (2H, m), 1.88 (1H, m), 0.92 (6H, d, J=7 Hz)

EXAMPLE 58

The procedure of Ex. 1 was repeated except that (E)-3-(4-methoxycinnamoyl)indole obtained in Pre. Ex. 28 was used in place of 3-heptanoylindole to give (E)-ethyl 4-[3-(4-methoxycinnamoyl)-1-indolyl]butyrate.

$^1$H-NMR (CDCl$_3$, 200 MHz) δ: 8.54 (1H, m), 7.80 (1H, d, J=16 Hz), 7.62 (2H, d, J=8.5 Hz), 7.2–7.45 (4H, m), 6.95 (2H, d, J=8.5 Hz), 4.29 (2H, t, J=7 Hz), 4.15 (2H, q, J=7 Hz), 3.86 (3H, s), 2.15–2.4 (4H, m), 1.25 (3H, t, J=7 Hz),

EXAMPLE 59

The procedure of Ex. 16 was repeated except that (E)-ethyl 4-[3-(4-methoxycinnamoyl)-1-indolyl]butyrate obtained in Ex. 58 was used in place of ethyl 4-[3-[8-(4-isobutylphenyl)-undecanoyl]-1-indolyl]butyrate to give (E)-4-[3-(4-methoxycinnamoyl-1-indolyl]butyric acid.

$^1$H-NMR (DMSO-d$_6$, 200 MHz) δ: 8.76 (1H, s), 8.35 (1H, m), 7.5–7.85 (5H, m), 7.15–7.4 (2H, m), 7.02 (2H, d, J=8.5 Hz), 4.30 (2H, t, J=7 Hz), 3.82 (3H, s), 2.29 (2H, t, J=7 Hz), 2.08 (2H, m)

EXAMPLE 60

The procedure of Ex. 1 was repeated except that (E)-3-cinnamoylindole obtained in Pre. Ex. 29 was used in place of 3-heptanoylindole to give (E)-ethyl 4-(3-cinnamoyl-1-indolyl)butyrate.

$^1$H-NMR (CDCl$_3$, 200 MHz) δ: 8.53 (1H, m), 7.92 (1H, s), 7.83 (1H, d, J=16 Hz), 7.6–7.7 (2H, m), 7.25–7.5 (8H, m), 4.30 (2H, t, J=7 Hz), 4.15 (2H, q, J=7 Hz), 2.15–2.4 (4H, m), 1.27 (3H, t, J=7 Hz),

EXAMPLE 61

The procedure of Ex. 16 was repeated except that (E)-ethyl 4-(3-cinnamoyl-1-indolyl)butyrate obtained in Ex. 60 was used in place of ethyl 4-[3-[8-(4-isobutylphenyl)undecanoyl]-1-indolyl]butyrate to give (E)-4-(3-cinnamoyl-1-indolyl)butyric acid.

$^1$H-NMR (DMSO-d$_6$, 200 MHz) δ: 8.81 (1H, s), 8.36 (1H, m), 7.2–7.9 (10H, m), 4.32 (2H, t, J=7 Hz), 2.81 (2H, t, J=7 Hz), 2.10 (2H, m)

EXAMPLE 62

A mixture of nonyl indole-3-carboxylate (251 mg) obtained in Pre. Ex. 30, benzyl 4-bromobutyrate (449 mg) and potassium carbonate (362 mg) in N,N-dimethylformamide was stirred at 50° C. for 6 hours. Water was added to the reaction mixture and the mixture was extracted with ethyl acetate, washed with water and brine, dried over magnesium sulfate and concentrated. Silica gel column chromatography of the concentrate afforded benzyl 4-(3-nonyloxycarbonyl-1-indolyl)butyrate (374 mg) as an oil.

$^1$H-NMR (CDCl$_3$, 200 MHz) δ: 8.17 (1H, m), 7.79 (1H, s), 7.2–7.45 (8H, m), 5.12 (2H, s), 4.32 (2H, t, J=7 Hz), 4.22 (2H, t, J=7 Hz), 2.37 (2H, t, J=7 Hz), 2.20 (2H, m), 1.80 (2H, m), 1.15–1.6 (12H, m), 0.88 (3H, t, J=7 Hz)

EXAMPLE 63

A mixture of benzyl 4-(3-nonyloxycarbonyl-1-indolyl)butyrate (368 mg) obtained in Ex. 62 and 10% palladium carbon (0.10 g) in methanol and 1,4-dioxane was stirred at room temperature for 2 hours under a hydrogen atmosphere at 3 atm. Removal of the catalyst and evaporation of the solvent afforded 4-(3-nonyloxycarbonyl-1-indolyl)butyric acid (246 g) as a solid.

$^1$H-NMR (CDCl$_3$, 200 MHz) δ: 8.17 (1H, m), 7.84 (1H, s), 7.2–7.45 (3H, m), 4.15–4.4 (4H, m), 2.40 (2H, t, J=7 Hz), 2.21 (2H, m), 1.80 (2H, m), 1.15–1.6 (12H, m), 0.88 (3H, t, J=7 Hz)

EXAMPLE 64

To a solution of 1-(3-ethoxycarbonylpropyl)indole-3-carboxylic acid (125 mg) obtained in Pre. Ex. 31 in dichloromethane was added oxalyl chloride and one drop of N,N-dimethylformamide. The mixture was stirred at room temperature for 1 hour and concentrated. The residue was dissolved in dichloromethane and to the solution was added a solution of nonylamine in dichloromethane. After being stirred at room temperature for 1 hour, water was added thereto and the mixture was extracted with ethyl acetate. The organic layer was washed with water and brine, dried over magnesium sulfate and concentrated. Silica gel column chromatography of the concentrate afforded ethyl 4-(3-nonylcarbamoyl-1-indolyl)butyrate as an oil.

$^1$H-NMR (CDCl$_3$, 200 MHz) δ: 7.92 (1H, m), 7.69 (1H, s), 7.2–7.45 (3H, m), 5.93 (1H, m), 4.23 (2H, t, J=7 Hz), 4.13 (2H, q, J=7 Hz), 3.50 (2H, q, J=7 Hz), 2.1–2.35 (4H, m), 1.15–1.75 (14H, m), 0.88 (3H, t, J=7 Hz)

EXAMPLE 65

To a solution of ethyl 4-(3-nonylcarbamoyl-1-indolyl)butyrate (124 mg) obtained in Ex. 64 in ethanol and 1,4-dioxane was added in aqueous solution of sodium hydroxide. After being stirred at room temperature for 2 hours, the mixture was concentrated, acidified with diluted hydrochloric acid, and extracted with ethyl acetate. The organic layer was washed with water and brine, dired over magnesium sulfate and concentrated to give 4-(3-nonylcarbamoyl-1-indolyl)butyric acid (96 mg) as an oil.

$^1$H-NMR (CDCl$_3$, 200 MHz) δ: 7.89 (1H, s), 7.82 (1H, m), 7.2–7.45 (3H, m), 6.10 (1H, m), 4.23 (2H, t, J=7 Hz), 3.50 (2H, q, J=7 Hz), 2.35 (2H, t, J=7 Hz), 2.18 (2H, m), 1.15–1.75 (14H, m), 0.88 (3H, t, J=7 Hz)

We claim:
1. A compound of the formula:

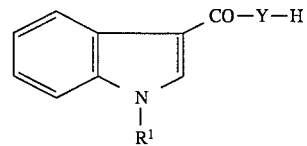

wherein

R$^1$ is a carboxy(lower)alkyl, and

Y is a (C$_4$–C$_{16}$)alkylene.

2. A pharmaceutical composition comprising a compound of claim 1 or a pharmaceutically acceptable salt thereof in association with pharmaceutically acceptable carriers or excipients.

3. A method for treating or preventing testosterone 5α-reductase-mediated diseases, which comprises administering a compound of claim 1 or a pharmaceutically acceptable salt thereof to human beings or animals.

4. A method for inhibiting testosterone 5α-reductase in humans or animals, which comprises administering a compound of claim 1 or a pharmaceutically acceptable salt thereof to human beings or animals.

\* \* \* \* \*